(12) United States Patent
Chen et al.

(10) Patent No.: US 10,745,729 B2
(45) Date of Patent: *Aug. 18, 2020

(54) METHODS FOR PRODUCING RECOMBINANT GLYCOPROTEINS WITH MODIFIED GLYCOSYLATION

(71) Applicant: Oneness Biotech Co. Ltd., Taipei (TW)

(72) Inventors: Nien-Yi Chen, New Taipei (TW); Che-Haorz Wu, New Taipei (TW); Hung-Chi Chen, Taipei (TW); Winston Town, Taipei (TW)

(73) Assignee: Oneness Biotech Co. Ltd., Taipei (TW)

( * ) Notice: Subject to any disclaimer, the term of this patent is extended or adjusted under 35 U.S.C. 154(b) by 94 days.

This patent is subject to a terminal disclaimer.

(21) Appl. No.: 15/358,497

(22) Filed: Nov. 22, 2016

(65) Prior Publication Data

US 2017/0145463 A1 May 25, 2017

Related U.S. Application Data

(63) Continuation of application No. 14/660,011, filed on Mar. 17, 2015, now Pat. No. 9,540,673.

(60) Provisional application No. 61/954,337, filed on Mar. 17, 2014.

(51) Int. Cl.
| | |
|---|---|
| *C12P 21/00* | (2006.01) |
| *C07K 16/42* | (2006.01) |
| *C07K 16/28* | (2006.01) |
| *C12N 9/24* | (2006.01) |
| *C07K 16/00* | (2006.01) |

(52) U.S. Cl.
CPC ............ *C12P 21/005* (2013.01); *C07K 16/00* (2013.01); *C07K 16/2887* (2013.01); *C07K 16/4291* (2013.01); *C12N 9/2402* (2013.01); *C12N 9/2405* (2013.01); *C12Y 302/01051* (2013.01); *C12Y 302/01096* (2013.01); *C07K 2317/14* (2013.01); *C07K 2317/41* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 6,602,684 B1 | 8/2003 | Umana et al. | |
| 2010/0003742 A1 | 1/2010 | Kim et al. | |
| 2010/0173323 A1* | 7/2010 | Strome | C07K 16/2863 435/7.1 |
| 2011/0318340 A1 | 12/2011 | Collin et al. | |

FOREIGN PATENT DOCUMENTS

| | | |
|---|---|---|
| EP | 2141237 A1 | 1/2010 |
| RU | 2479629 C2 | 4/2013 |
| WO | WO 1999/54342 A1 | 10/1999 |
| WO | WO 2008/071418 A2 | 6/2008 |
| WO | WO 2013/120066 A1 | 8/2013 |

OTHER PUBLICATIONS

Yamane-Ohnuki et al. Biotech and Bioeng. 2004, 87(5)614-622 (Year: 2004).*
Bailey et al., Engineering Glycosylation in Animal Cells. New Develop. New Appl. Animal Cell Tech. 2002:5-23.
Butchard et al., Fluorocarbohydrates—XXVII1: 2-deoxy-2-fluoro-1-fucose: synthesis and structure. Tetrahedron. 1979;35(21):2551-2554.
Cerdeño-Tárraga et al., Extensive DNA inversions in the B. fragilis genome control variable gene expression. Science. Mar. 4, 2005;307(5714):1463-5.
Collin et al., Effect of SpeB and EndoS from *Streptococcus pyogenes* on human immunoglobulins. Infect Immun. Nov. 2001;69(11):7187-9.
Collin et al., EndoS, a novel secreted protein from *Streptococcus pyogenes* with endoglycosidase activity on human IgG. EMBO J. Jun. 15, 2001;20(12):3046-55.
Bielicki et al., Recombinant canine alpha-1-fucosidase: expression, purification, and characterization. Mol Genet Metab. Jan. 2000;69(1):24-32.
Cumming, Glycosylation of recombinant protein therapeutics: control and functional implications. Glycobiology. Mar. 1991;1(2):115-30.
Ferrara et al., Modulation of therapeutic antibody effector functions by glycosylation engineering: influence of Golgi enzyme localization domain and co-expression of heterologous beta 1, 4-N-acetylglucosaminyltransferase III and Golgi alpha-mannosidase II. Biotechnol Bioeng. Apr. 5, 2006;93(5):851-61.
Fukushima et al., Molecular cloning of a cDNA for human alpha-L-fucosidase. Proc Natl Acad Sci U S A. Feb. 1985;82(4):1262-5.
Gerdes et al., GA201 (RG7160): a novel, humanized, glycoengineered anti-EGFR antibody with enhanced ADCC and superior in vivo efficacy compared with cetuximab. Clin Cancer Res. Mar. 1, 2013;19(5):1126-38. doi: 10.1158/1078-0432.CCR-12-0989. Epub Dec. 3, 2012.
Huhn et al., IgG glycosylation analysis. Proteomics. Feb. 2009;9(4):882-913. doi: 10.1002/pmic.200800715.
Imperiali et al., Effect of N-linked glycosylation on glycopeptide and glycoprotein structure. Curr Opin Chem Biol. Dec. 1999;3(6):643-9.
Jefferis, Glycosylation as a strategy to improve antibody-based therapeutics. Nat Rev Drug Discov. Mar. 2009;8(3):226-34. doi: 10.1038/nrd2804.
Jefferis, Recombinant antibody therapeutics: the impact of glycosylation on mechanisms of action. Trends Pharmacol Sci. Jul. 2009;30(7):356-62. doi:10.1016/j.tips.2009.04.007. Epub Jun. 22, 2009.

(Continued)

Primary Examiner — James D Schultz
(74) Attorney, Agent, or Firm — Polsinelli PC

(57) ABSTRACT

Genetically engineered host animal cells capable of producing glycoproteins having modified glycosylation patterns, e.g., defucosylation and/or monoglycosylation. Such host animal cells can be engineered to express fucosidase, endoglycosidase or both.

23 Claims, 8 Drawing Sheets

Specification includes a Sequence Listing.

(56) References Cited

OTHER PUBLICATIONS

Jiang et al., Advances in the assessment and control of the effector functions of therapeutic antibodies. Nat Rev Drug Discov. Feb. 2011;10(2):101-11. doi: 10.1038/nrd3365.

Kapur et al., A prominent lack of IgG1-Fc fucosylation of platelet alloantibodies in pregnancy. Blood. Jan. 23, 2014;123(4):471-80. doi: 10.1182/blood-2013-09-527978. Epub Nov. 15, 2013.

Kim et al., Enzymatic deglycosylation of glycoproteins. Methods Enzymol. 2013;533:259-63. doi: 10.1016/B978-0-12-420067-8.00019-2 (Abstract only).

Liu et al., Role for alpha-L-fucosidase in the control of Helicobacter pylori-infected gastric cancer cells. Proc Natl Acad Sci U S A. Aug. 25, 2009;106(34):14581-6. doi: 10.1073/pnas.0903286106. Epub Aug. 7, 2009.

Patterson, Metabolic mimics: the disorders of N-linked glycosylation. Semin Pediatr Neurol. Sep. 2005;12(3):144-51.

Raju, Terminal sugars of Fc glycans influence antibody effector functions of IgGs. Curr Opin Immunol. Aug. 2008;20(4):471-8. doi: 10.1016/j.coi.2008.06.007. Epub Jul. 17, 2008.

Shields et al., Lack of fucose on human IgG1 N-linked oligosaccharide improves binding to human Fcgamma RIII and antibody-dependent cellular toxicity. J Biol Chem. Jul. 26, 2002;277(30):26733-40. Epub May 1, 2002.

Sinclair et al., Glycoengineering: the effect of glycosylation on the properties of therapeutic proteins. J Pharm Sci. Aug. 2005;94(8):1626-35.

Winterbourne et al., 2-Deoxy-2-Fluro-L-Fucose and its effect on L-[1-$^{14}$c] fucose utilization in mammalian cells. Biochem. Biophys. Res. Comm. Apr. 27, 1979. 87(4):989-992.

Xu et al., The genomic sequence of the Chinese hamster ovary (CHO)-K1 cell line. Nat Biotechnol. Jul. 31, 2011;29(8):735-41. doi: 10.1038/nbt.1932.

Yamane-Ohnuki et al., Production of therapeutic antibodies with controlled fucosylation. MAbs. May-Jun. 2009;1(3):230-6. Epub May 28, 2009.

Yazawa et al., alpha-L-fucosidase from aspergillus niger: demonstration of a novel alpha-L-(1-6)-fucosidase acting on glycopeptides. Biochem Biophys Res Commun. Apr. 29, 1986;136(2):563-9.

* cited by examiner

A.

B.

C.

A.

B.

| Kozak | Secretory Signal | Fucosidase / Endoglycosidase | Tag |

B.

METHODS FOR PRODUCING RECOMBINANT GLYCOPROTEINS WITH MODIFIED GLYCOSYLATION

CROSS-REFERENCE TO RELATED APPLICATION

This application is a continuation of U.S. application Ser. No. 14/660,011, filed Mar. 17, 2015, which claims the benefit of U.S. Provisional Application No. 61/954,337, filed on Mar. 17, 2014, the content of each of which is hereby incorporated by reference in its entirety.

BACKGROUND OF THE INVENTION

Glycosylation is important to the structures and functions of glycoproteins. For example, glycosylation is suggested to affect protein folding (and thus stability) and/or bioactivities of glycoproteins. The demand of therapeutic recombinant glycoproteins, especially monoclonal antibodies, robustly grows in the recent two decades. Previous studies reveal that minor differences in glycan structures of recombinant glycoproteins may impact on the biological activities and pharmacokinetics of the glycoproteins. For example, Darbepoetin alfa is a hyper-glycosylated analog of recombinant human erythropoietin (EPO) with two extra N-linked glycosylation sites. The extra N-glycosylation increases the percentage of the molecular mass in carbohydrates and significantly extends the serum half-life of Darbepoetin alfa, as compared to endogenous and recombinant EPO. In addition, for a therapeutic antibody whose efficacy mainly relies on antibody-dependent cell cytotoxicity (ADCC), both chemo-enzymatic and genetic approaches to remove the core fucose residue on the Fc portion have been developed to increase the potency of the ADCC effect induced by that antibody.

However, currently available methods for remodeling glycosylation often require multiple enzymes and/or multiple steps, resulting in high costs for manufacturing glyco-engineered recombinant proteins.

SUMMARY OF THE INVENTION

The present disclosure is based on the development of genetically engineered host animal cells capable of producing glycoproteins such as antibodies having modified glycosylation, including defucosylation and monoglycosylation. Such host animal cells were engineered to overly express one or more of fucosidases, endoglycosidases, or both. Unexpectedly, changes to the cellular glycosylation machinery in the host animal cells did not result in adverse effects in relation to glycoprotein synthesis and host cell growth.

Accordingly, the present disclosure provides a genetically engineered host animal cell (e.g., a mammalian cell), which overly expresses a fucosidase, an endoglycosidase, or both, wherein the host animal cell produces glycoproteins having modified glycosylation as compared with the wild-type couterpart. In some examples, the fucosidase can be a mammalian fucosidase or a bacterial fucosidase, for example, human FUCA1, human FUCA2, *Cricetulus griseus* fucosidase, alpha-L-1 *Chryseobacterium meningosepticum* α1,6-fucosidase, or bacterial fucosidase BF3242. Alternatively or in addition, the endoglycosidase can be an Endo S enzyme, e.g., an enzyme comprising the amino acid sequence of SEQ ID NO:11. In some examples, the genetically engineered host animal cell expresses (i) human FUCA1, human FUCA2, *Cricetulus griseus* fucosidase, alpha-L-1 *Chryseobacterium meningosepticum* α1,6-fucosidase, or bacterial fucosidase BF3242, and (ii) an Endo S (such as SEQ ID NO:11).

The genetically engineered host animal cell described herein may further express a glycoprotein, which can be exogenous (not expressed in the native animal cell of the same type). Examples include, but are not limited to, an antibody, an Fc-fusion protein, a cytokine, a hormone, a growth factor, or an enzyme.

In some examples, the genetically engineered host animal cell is a mammalian cell, e.g., a Chinese hamster ovary (CHO) cell, a rat myeloma cell, a baby hamster kidney (BHK) cell, a hybridoma cell, a Namalwa cell, an embryonic stem cell, or a fertilized egg.

Also described herein are methods for producing glycoproteins having modified glycosylation patterns (e.g., defucosylated or mono-glycosylated) using any of the genetically engineered host animal cells described herein. The method may comprise (i) providing a host animal cell expressing (a) a glycoprotein, and (b) a fucosidase, an endoglycosidase, or both; culturing the host animal cell under conditions allowing for producing the glycoprotein and the fucosidase, the endoglycosidase, or both; (ii) collecting the host animal cell or the culturing supernatant for isolating the glycoprotein, and optionally (iii) isolating the glycoprotein. The method may further comprise (iv) analyzing the glycosylation pattern of the glycoprotein.

Further, the present disclosure features a method for preparing any of the genetically engineered host animal cells described herein. The method may comprise (i) introducing into an animal cell one or more expression vectors, which collectively encode a fucosidase, an endoglycosidase, or both, and optionally (ii) introducing into the animal cell an expression vector encoding a glycoprotein. The method may further comprise selecting transformed cells expressing the fucosidase, the endoglycosidase, and the glycoprotein.

The details of one or more embodiments of the invention are set forth in the description below. Other features or advantages of the present invention will be apparent from the following drawings and detailed description of several embodiments, and also from the appended claims.

DETAILED DESCRIPTION OF THE INVENTION

Disclosed herein are genetically engineered host animal cells such as mammalian cells capable of producing glycoproteins (e.g., exogenous glycoproteins such as antibodies) having modified glycosylation patterns (e.g., modified N-glycosylation patterns such as defucosylated N-glycans or mono-sugar glycans). Such host animal cells may be engineered to overly express a fucosidase, an endoglycosidase, or both. Optionally, the host animal cell is also engineered to express an exogenous glycoprotein such as an antibody.

Figure 1:
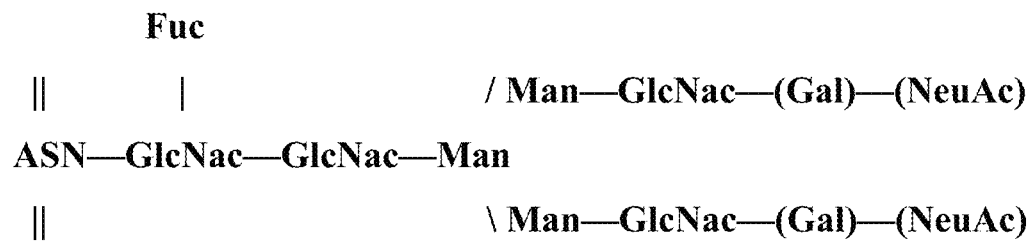
FIG. 1 is a schematic illustration showing the structures of various N-glycans. A: typical N-linked glycans of glycoproteins. B: defucosylated N-glycans. C: N-glycans having a mono-Nacetylglucosamine reducing sugar (monoglycosylated).
Figure 1:
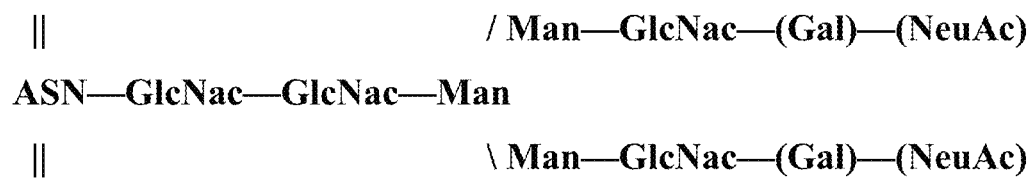
Figure 1:
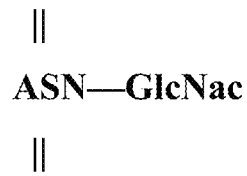

The structure of a typical complex N-glycan of glycoproteins produced in wild-type mammalian cells is shown in FIG. 1, panel A. Such a complex N-glycan contains a N-acetylglucosamine (GlcNAc) residue attached to a glycosylation site, an asparagine residue (Asn) of a glycoprotein, and a fucose residue is attached to that Asn residue in an alpha1,6-linkage. The genetically engineered host animal cells are capable of producing glycoproteins (e.g., endogenous or exogenous) having modified N-glycans, such as defucosylated N-glycans, an example of which is provided in FIG. 1, panel B, and mono-sugar N-glycans, in which only a GlcNAc residue is attached to the Asn glycosylation site (FIG. 1, panel C). A glycoprotein having modified glycosylation refers to a glycoprotein carrying at least one glycan such as an N-glycan that is structurally different from glycans of the glycoprotein produced in the wild-type counterpart of the genetically engineered host animal cell. A defucosylated glycan refers to any glycan that does not contain an alpha1,6-fucose residue or any fucose residue.

A. Fucosidase

A fucosidase is an enzyme that breaks down fucose. This enzyme cleaves fucose residues from a glycan containing such. The fucosidase for use in making the genetically engineered host animal cells can be a mammalian fucosidase or a bacterial fucosidase. In some embodiments, the fucosidase is a wild-type enzyme, e.g., a wild-type bacterial enzyme or a wild-type mammalian enzyme such as a human enzyme. The amino acid sequences and encoding nucleotide sequences of a number of exemplary fucosidases are provided below (including a His-tag at the C-terminus):

```
Human Fucosidase FUCA1
Amino Acid Sequence
                                              (SEQ ID NO: 1)
MRVPAQLLGLLLLWLPGARCQPPRRYTPDWPSLDSRPLPAWFDEAKFGVFIHWGVFSVPA

WGSEWFWWHWQGEGRPQYQRFMRDNYPPGFSYADFGPQFTARFFHPEEWADLFQAAGAKY

VVLTTKHHEGFTNWPSPVSWNWNSKDVGPHRDLVGELGTALRKRNIRYGLYHSLLEWFHP

LYLLDKKNGFKTQHFVSAKTMPELYDLVNSYKPDLIWSDGEWECPDTYWNSTNFLSWLYN

DSPVKDEVVVNDRWGQNCSCHHGGYYNCEDKFKPQSLPDHKWEMCTSIDKFSWGYRRDMA

LSDVTEESEIISELVQTVSLGGNYLLNIGPTKDGLIVPIFQERLLAVGKWLSINGEAIYA

SKPWRVQWEKNTTSVWYTSKGSAVYAIFLHWPENGVLNLESPITTSTTKITMLGIQGDLK

WSTDPDKGLFISLPQLPPSAVPAEFAWTIKLTGVKHHHHHH

Nucleotide Sequence
                                     (SEQ ID NO: 2; codon optimized)
atgagagtgcctgctcagctgctgggactgctgctgctgtggctgcctggtgctagatgc cagccccctcggagatacaccectgactggccttccctggactccagacctctgcccgct tggtttgacgaggccaagttcggcgtgttcatccactggggcgtgttctccgtgcctgcc tggggctctgagtggttctggtggcattggcagggcgagggcagacctcagtaccagcgg ttcatgcgggacaactaccccctggcttctcctacgccgacttcggccctcagttcacc gcccggttcttccaccctgaggaatgggccgatctgttccaggccgctggcgccaaatac gtggtgctgaccaccaagcaccacgagggcttcaccaactggccctcccccgtgtcctgg aactggaactctaaggacgtgggccccaccgggatctcgtgggagaactgggaaccgcc ctgcggaagcggaacatcagatacggcctgtaccactccctgctggaatggttccacccc ctgtacctgctggacaagaagaacggcttcaagacccagcacttcgtgtccgccaagacc atgcccgagctgtacgacctcgtgaactcctacaagcccgacctgatttggagcgacggc
```

-continued

```
gagtgggagtgccccgacacctattggaactccaccaactttctgtcctggctgtacaac gactcccctgtgaaggacgaggtggtcgtgaacgacagatggggccagaactgctcctgt caccacggcggctactacaactgcgaggacaagttcaagcccagtccctgcccgaccac aagtgggagatgtgcacctctatcgacaagttctcctggggctaccggcgggacatggcc ctgtctgatgtgaccgaggaatccgagatcatctccgagctggtgcagaccgtgtccctg ggcggcaactacctgctgaacatcggccctaccaaggacggcctgatcgtgcccatcttc caggaacggctgctggccgtgggcaagtggctgtctatcaacggcgaggccatctacgcc tccaagccttggcgagtgcagtgggagaagaacaccacctccgtgtggtacacctccaag ggctctgccgtgtacgccatcttcctgcactggcccgagaacggcgtgctgaacctggaa tcccccatcaccacctctaccaccaagatcaccatgctgggcatccagggcgacctgaag tggtccaccgaccctgacaagggcctgttcatctccctgccccagctgcctccttccgct gtgcctgctgagttcgcctggaccatcaagctgaccggcgtgaagcaccaccaccatcac cattga
```

Human Fucosidase FUCA2:
Amino Acid Sequence
(SEQ ID NO: 3)
MRVPAQLLGLLLLWLPGARCHSATRFDPTWESLDARQLPAWFDQAKFGIFIHWGVFSVPS

FGSEWFWWYWQKEKIPKYVEFMKDNYPPSFKYEDEGPLFTAKFFNANQWADIFQASGAKY

IVLTSKHHEGFTLWGSEYSWNWNAIDEGPKRDIVKELEVAIRNRTDLRFGLYYSLFEWFH

PLFLEDESSSFHKRQFPVSKTLPELYELVNNYQPEVLWSDGDGGAPDQYWNSTGFLAWLY

NESPVRGTVVTNDRWGAGSICKHGGFYTCSDRYNPGHLLPHKWENCMTIDKLSWGYRREA

GISDYLTIEELVKQLVETVSCGGNLLMNIGPTLDGTISVVFEERLRQMGSWLKVNGEAIY

ETHTWRSQNDTVTPDVWYTSKPKEKLVYAIFLKWPTSGQLFLGHPKAILGATEVKLLGHG

QPLNWISLEQNGIMVELPQLTIHQMPCKWGWALALTNVIHHHHHH

Nucleotide Sequence
(SEQ ID NO: 4; codon optimized)

```
atgagagtgcctgctcagctgctgggactgctgctgctgtggctgcctggcgctagatgc cactccgccaccagattcgaccccacctgggagtctctggacgccagacagctgcccgct tggtttgaccaggccaagttcggcatcttcatccactggggcgtgttctccgtgcccagc ttcggctctgagtggttctggtggtactggcagaaagagaagatccccaaatacgtggag ttcatgaaggacaactaccccccagcttttaagtacgaggacttcggccccctgttcacc gccaagttcttcaacgccaaccagtgggccgacatcttccaggcctctggcgccaagtac atcgtgctgacctccaagcaccacgagggcttcaccctgtggggctccgagtactcctgg aactggaacgccatcgacgagggccccaagcgggacatcgtgaaagaactggaagtggcc atccggaaccggaccgacctgagattcggcctgtactactccctgttcgagtggttccac cccctgtttctggaagatgagtcctccagcttccacaagcggcagttccccgtgtccaag accctgcccgagctgtacgagctcgtgaacaactaccagcccgaggtgctgtggagtgac ggggatggtggtgcccccgatcagtactggaactctaccggcttcctggcctggctgtac aacgagtctcctgtgcggggcaccgtcgtgaccaacgatagatggggcgctggctccatc tgcaagcacggcggcttctacacctgttccgaccggtacaacccccggccatctgctgcct cacaagtgggagaactgcatgaccatcgacaagctgtcctggggctacagaagagaggcc ggcatctccgactacctgacaatcgaggaactcgtgaagcagctggtggaaaccgtgtcc tgcggcggcaacctgctgatgaacatcggccctaccctggacggcaccatctccgtggtg
```

-continued

```
ttcgaggaacggctgcggcagatgggctcctggctgaaagtgaacggcgaggccatctac gagacacacacctggcggtcccagaacgacaccgtgaccccttgacgtgtggtacaccagc
```

```
ttcgaggaacggctgcggcagatgggctcctggctgaaagtgaacggcgaggccatctac
gagacacacacctggcggtcccagaacgacaccgtgaccccttgacgtgtggtacaccagc
aagcccaaagaaaagctggtgtatgccatcttcctgaagtggcctacctccggccagctg
ttcctgggccacccttaaggctatcctgggcgccaccgaagtgaaactgctgggccatgga
cagcccctgaactggatctccctggaacagaacggcatcatggtggaactgccccagctg
accatccatcagatgccctgcaaatggggctgggccctggccctgaccaacgtgatccac
catcaccaccaccactga
```

*Cricetulus griseus* (Chinese Hamster) Fucosidase FUCA2
Amino Acid Sequence
(SEQ ID NO: 5)

```
MRVPAQLLGLLLLWLPGARCKSSRRYDPTWESLDRRPLPSWFDQAKEGIFIHWGVFSVPS
FGSEWFWWYWQKEKRPKFVDFMNNNYPPGFKYEDFGVLFTAKFFNASQWADILQASGAKY
LVLTSKHHEGFTLWGSEYSWNWNAVDEGPKRDIVKELKVAITKNTDLRFGLYYSLFEWFH
PLFLEDKLSSFQKRQFPISKMLPELYELVNKYQPDILWTDGDGGAPDRYWNSTGFLAWLY
NESPVRNTVVTNDRWGAGSICKHGGYYTCSDRYNPGHLLPHKWENCMTIDQFSWGYRREA
VISDYLTIEELVKQLVETVACGGNLLMNIGPTLDGIIPVIFEERLRQMGMWLKVNGEAIY
ETQPWRSQNDTATPDVWYTYKPEEKIVYAIFLKWPVSRELFLEQPIGSLGETEVALLGEG
KPLTWTSLKPNGIIVELPQLTLHQMPCKWGWTLALTNVTHHHHHH
```

Nucleotide Sequence
(SEQ ID NO: 6; codon optimized)

```
atgagagtgcctgctcagctgctgggactgctgctgctgtggctgcctggcgctagatgc
aagtcctctcggagatacgaccccacctgggagtccctggacagaaggcctctgcccagt
tggttcgaccaggccaagttcggcatcttcatccactggggcgtgttctccgtgcccagc
ttcggctctgagtggttctggtggtactggcagaaagagaagcggcccaagttcgtggac
ttcatgaacaacaactaccccctggctttaagtacgaggacttcggcgtgctgttcacc
gccaagttcttcaacgcctcccagtgggccgacatcctgcaggcttccggcgctaagtac
ctggtgctgacctccaagcaccacgagggctttaccctgtggggctccgagtactcctgg
aactggaacgccgtggacgagggccctaagcgggacatcgtgaaagaactgaaggtggcc
atcaccaagaacaccgacctgagattcggcctgtactactccctgttcgagtggttccac
cccctgtttctggaagataagctgtccagcttccagaagcggcagttccccatctccaag
atgctgcccgagctgtacgagctcgtgaacaagtaccagcctgacatcctgtggaccgac
ggggatggtggcgcccctgacagatactggaactctaccggcttcctggcctggctgtac
aacgagtcccctgtgcggaacaccgtcgtgaccaacgacagatggggcgctggctccatc
tgcaagcacggcggctactacacctgttccgaccggtacaaccccggccatctgctgcct
cacaagtgggagaactgcatgacaatcgaccagttctcctggggctaccggcgcgaggcc
gtgatctctgactacctgaccatcgaggaactcgtgaagcagctggtggaaaccgtggcc
tgtggcggcaacctgctgatgaacatcggccctacctggacggcatcatccccgtgatc
ttcgaggaacggctgcggcagatgggcatgtggctgaaagtgaacggcgaggccatctac
gagacacagccttggcggtcccagaacgacaccgccacacctgacgtgtggtacacctac
aagcccgaagagaagatcgtgtacgccatcttcctgaagtggcccgtgtccagagagctg
tttctggaacagcccatcggctccctgggcgagacagaagtggctctgctgggcgagggc
```

-continued aagcctctgacctggacctccctgaagcccaatggcatcatcgtggaactgccccagctg accctgcaccagatgccctgtaaatggggctggaccctggccctgaccaacgtgacccac caccaccatcaccactga

*Chryseobacterium meningosepticum* α1,6-Fucosidase
Amino Acid Sequence
(SEQ ID NO: 7)
MRVPAQLLGLLLLWLPGARCHNVSEGYEKPADPLVVQNLEQWQDLKFGLFMHWGTYSQWG

IVESWSLCPEDESWTQRKPEHGKSYNEYVKNYENLQTTFNPVQFNPQKWADATKKAGMKY

VVFTTKHHDGFAMFDTKQSDYKIISSKTPFSKNPKADVAKEIENTERDNGFRIGAYESKP

DWHSDDYWWSYFPPKDRNVNYDPQKYPARWENFKKFTENQLNEITSNYGKIDILWLDGGW

VRPFHTIDPNIEWQRTIKVEQDIDMDKIGTMARKNQPGIIIVDRTVPGKWENYVTPEQAV

PEHALSIPWESCITMGDSFSYVPNDNYKSSQKIIETLIRIISRGGNYLMNIAPGPNGDYD

AVVYERLKEISGWMDKNQSAVETTRALAPYHESDFYYTQSKDGKIVNVFHISEKSNYQAP

SELSFSIPENINPKTVKVLGISSQIKWKKKGNKIHVQLPEERTKLNYSTVIQITQHHHHH

H

Nucleotide Sequence
(SEQ ID NO: 8; codon optimized)
atgagagtgcctgctcagctgctgggactgctgctgctgtggctgcctggcgctagatgc cacaatgtgtccgagggctacgagaagcccgccgaccctctggtggtgcagaacctggaa cagtggcaggacctgaagttcggcctgttcatgcactggggcacctactcccagtggggc atcgtggaatcctggtcctgtgccctgaggacgagtcttggacccagcggaagcctgag cacggcaagtcctacaacgagtacgtgaagaactacgagaacctgcagaccaccttcaac cccgtgcagttcaaccccagaagtgggccgacgccaccaagaaagccggcatgaaatac gtggtgttcaccaccaagcaccacgacggcttcgccatgttcgacaccaagcagtccgac tacaagatcacctcctccaagacccccttcagcaagaaccccaaggccgacgtggccaaa gagattttcaacaccttccgggacaacggcttccggatcggcgcctacttctccaagcct gactggcactccgacgactactggtggtcctacttcccacccaaggaccggaacgtgaac tacgaccctcagaaatacccgccagatgggagaacttcaagaagttccccttcaatcag ctgaacgagatcaccagcaactacggcaagatcgacatcctgtggctggacggcggatgg gtgcgacccttccacaccatcgaccccaacatcgagtggcagcggaccatcaaggtggaa caggacatcgacatggacaagatcggcaccatggcccggaagaaccagcccggcatcatc atcgtggaccggaccgtgcctggcaagtgggagaattacgtgaccccgagcaggccgtg cctgagcatgccctgtctatcccttgggagtcctgtatcacaatgggcgacagcttctcc tacgtgcccaacgacaactacaagtcctcccagaagatcatcgagacactgatcaggatc atctccagaggcggcaactacctgatgaatatcgcccctggccccaacggcgactacgac gctgtggtgtacgagcggctgaaagaaatctccggctggatggataagaaccagtccgcc gtgtttaccacccgggctctggccccttaccacgagtccgacttctactacacccagtcc aaggacggaaagatcgtgaacgtgttccacatctccgagaagtccaactaccaggccccc tccgagctgtccttcagcatccccgagaacatcaaccccaagaccgtgaaggtgctgggc -continued

```
atctccagccagatcaagtggaagaagaagggcaacaagatccacgtgcagctgcccgag gaacggaccaagctgaactactccaccgtgatccagatcacccagcaccaccaccatcac cactga
```

Bacterial Fucosidase BF3242
Amino Acid Sequence (SEQ ID NO: 9)

```
MRVPAQLLGLLLLWLPGARCQQKYQPTEANLKARSEFQDNKFGIFLHWGLYAMLATGEWT

MTNNNLNYKEYAKLAGGFYPSKFDADKWVAAIKASGAKYICFTTRHHEGFSMFDTKYSDY

NIVKATPFKRDVVKELADACAKHGIKLHFYYSHIDWYREDAPQGRTGRRTGRPNPKGDWK

SYYQFMNNQLTELLTNYGPIGAIWFDGWWDQDINPDFDWELPEQYALIHRLQPACLVGNN

HHQTPFAGEDIQIFERDLPGENTAGLSGQSVSHLPLETCETMNGMWGYKITDQNYKSTKT

LIHYLVKAAGKDANLLMNIGPQPDGELPEVAVQRLKEVGEWMSKYGETIYGTRGGLVAPH

DWGVTTQKGNKLYVHILNLQDKALFLPIVDKKVKKAVVFADKTPVRETKNKEGIVLELAK

VPTDVDYVVELTIDHHHHHH
```

Nucleotide Sequence (SEQ ID NO: 10; codon optimized)

```
atgagagtgcctgctcagctgctgggactgctgctgctgtggctgcctggtgctagatgc cagcagaagtaccagcccaccgaggccaacctgaaggccagatccgagttccaggacaac aagttcggcatcttcctgcactggggcctgtacgccatgctggctactggcgagtggacc atgaccaacaacaacctgaactacaaagagtacgctaagctggctggcggcttctacccc tccaagttcgacgccgacaaatgggtggccgccatcaaggcctctggcgccaagtacatc tgcttcaccacccggcaccacgagggcttctccatgttcgacaccaagtactccgactac aacatcgtgaaggccacccccttcaagcgggacgtcgtgaaagagctggccgacgcctgc gctaagcacggcatcaagctgcacttctactactcccacatcgactggtacagagaggac gcccccagggcagaaccggcagaagaacaggcagacccaaccccaagggcgactggaag tcctactaccagtttatgaacaaccagctgaccgagctgctgaccaactacggccccatc ggcgccatttggttcgacggtggtgggaccaggacatcaaccccgacttcgactgggag ctgcccgagcagtacgccctgatccacagactgcagcccgcctgtctcgtgggcaacaac caccaccagacccccttgccggcgaggacatccagattttcgagcgggatctgcccggc gagaacaccgctggactgtctggccagtccgtgtcccatctgcccctggaaacctgcgag acaatgaacggcatgtggggctacaagatcaccgaccagaactacaagtccaccaagaca ctgatccactacctcgtgaaagccgctggcaaggacgccaacctgctgatgaacatcggc ccccagcctgacggcgagctgcctgaagtggctgtgcagcggctgaaagaagtgggagag tggatgtctaagtacggcgagactatctacggcaccagaggcggcctggtggcccctcat gattggggcgtgaccacccagaagggcaacaagctgtacgtgcacatcctgaacctgcag
```

-continued
```
gacaaggccctgttcctgcccatcgtggacaagaaagtgaagaaagccgtggtgttcgcc gacaagaccccgtgcggttcaccaagaacaaagagggcatcgtgctggaactggccaag gtgcccaccgacgtggactacgtggtggaactgaccatcgaccaccatcatcaccaccac tga
```

In some embodiments, the fucosidase can be an enzyme (e.g., a wild-type enzyme) that share at least 85% (e.g., 90%, 93%, 95%, 96%, 97%, 98%, or 99%) sequence identity as compared with any of the exemplary fucosidases provided above (e.g., SEQ ID NO:1, SEQ ID NO:3, SEQ ID NO:5, SEQ ID NO:7, or SEQ ID NO:9, as well as other fucosidases described herein).

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of the invention. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

Mammalian fucosidases that can be used in constructing the genetically engineered host animal cells include, but are not limited to, those disclosed under GenBank Accession Nos. NP_114409.2, XP_003811598.1, AAH03060.1, EHH53333.1, XP_001127152.1, XP_010360962.1, XP_006084558.1, XP_004263802.1, XP_007171384.1, XP_006075254.1, XP_010982011.1, NP_001004218.1, and XP_010964137.1.

Bacterial fucosidases that can be used in constructing the genetically engineered host animal cells include, but are not limited to, those disclosed under GenBank Accession Nos. WP_008769537.1, WP_032568292.1, EYA08300.1, WP_005780841.1, EXY26528.1, WP_044654435.1, WP_029425671.1, WP_022470316.1, CDA84816.1, WP_004307183.1, and WP_008025871.1.

B. Endoglycosidase

An Endoglycosidase is an enzyme that breaks the glycosidic bonds between two sugar monomers in a glycan, thereby releasing oligosaccharides from glycoproteins or glycolipids. Endoglycosidase for use in the present disclosure (e.g., a wild-type enzyme) includes endoglycosidase D, endoglycosidase F, endoglycosidase F1, endoglycosidase F2, endoglycosidase H, and endoglycosidase S. Exemplary endoglycosidase enzymes of each subgenus are provided in the table below:

| Entry | Entry name | Protein names | Gene names | Organism |
|---|---|---|---|---|
| P36911 | EBA1_ELIME | Endo-beta-N-acetylglucosaminidase F1 (EC 3.2.1.96) (Di-N-acetylchitobiosyl beta-N-acetylglucosaminidase F1) (Endoglycosidase F1) (Mannosyl-glycoprotein endo-beta-N-acetyl-glucosaminidase F1) | endOF1 | Elizabethkingia meningoseptica (Chryseobacterium meningosepticum) |
| P36913 | EBA3_ELIME | Endo-beta-N-acetylglucosaminidase F3 (EC 3.2.1.96) (Di-N-acetylchitobiosyl beta-N-acetylglucosaminidase F3) (Endoglycosidase F3) (Mannosyl-glycoprotein endo-beta-N-acetyl-glucosaminidase F3) | endOF3 | Elizabethkingia meningoseptica (Chryseobacterium meningosepticum) |
| P36912 | EBA2_ELIME | Endo-beta-N-acetylglucosaminidase F2 (EC 3.2.1.96) (Di-N-acetylchitobiosyl beta-N-acetylglucosaminidase F2) (Endoglycosidase F2) (Mannosyl-glycoprotein endo-beta-N-acetyl-glucosaminidase F2) | endOF2 | Elizabethkingia meningoseptica (Chryseobacterium meningosepticum) |
| P04067 | EBAG_STRPL | Endo-beta-N-acetylglucosaminidase H (EC 3.2.1.96) (DI-N-acetylchitobiosyl beta-N-acetylglucosaminidase H) (Endoglycosidase H) (Endo H) (Mannosyl-glycoprotein endo-beta-N-acetyl-glucosaminidase H) | | Streptomyces plicatus |
| T0JJ04 | T0JJ04_STRSZ | Endoglycosidase (EndoS) (EC 3.2.1.96) | M837_00287 | Streptococcus equi subsp. zooepidemicus SzS31A1 |

Other suitable endoglycosidase enzymes include those that share at least 85% (e.g., 90%, 95%, 98%, or 99%) sequence identity to an of the enzymes described herein. Enzymes having a high sequence homology (e.g., at least 85% sequence identity) with any of the above-listed endoglycosidase are expected to possess the same biological activity. Such enzymes (e.g., wild-type enzymes) may be retrieved from a gene database such as GenBank using one of the above listed enzymes as a query.

In some embodiments, the endoglycosidase described herein is an Endo S enzyme. Endo S is an endoglycosidase that specifically cleaves N-glycans at the first GlcNAc residues attached to the Asn glycosylation sites of Fc domains in native IgG molecules, resulting in monoglycosylated IgG molecules, i.e., an IgG molecule having a single GlcNAc attached to an Asn glycosylation site. The amino acid sequence and the encoding nucleotide sequence are provided below:

```
Endo S Amino Acid Sequence (SEQ ID NO: 11):
MRVPAQLLGLLLLWLPGARCAQHDSLIRVKAEDKVVQTSPSVSAIDDLHYLSENSKKEFK

EGLSKAGEVPEKLKDILSKAQQADKQAKVLAEMKVPEKIAMKPLKGPLYGGYFRTWHDKT

SDPAEKDKVNSMGELPKEVDLAFVFHDWTKDYSLFWQELATKHVPTLNKQGTRVIRTIPW

RFLAGGDHSGIAEDTQKYPNTPEGNKALAKAIVDEYVYKYNLDGLDVDIERDSIPKVNGK

ESNENIQRSIAVFEEIGKLIGPKGADKSRLFIMDSTYMADKNPLIERGAPYIDLLLVQVY

GIQGEKGDWDPVARKPEKTMEERWESYSKYIRPEQYMVGFSFYEENAGSGNLWYDINERK

DDHNPLNSEIAGTRAERYAKWQPKTGGVKGGIFSYAIDRDGVAHQPKKVSDDEKRTNKAI

KDITDGIVKSDYKVSKALKKVMENDKSYELIDQKDFPDKALREAVIAQVGSRRGDLERFN

GTLRLDNPDIKSLEGLNKLKKLAKLELIGLSQITKLDSSVLPENIKPTKDTLVSVLETYK

NDDRKEEAKAIPQVALTISGLTGLKELNLAGFDRDSLAGIDAASLTSLEKVDLSKNKLDL

AAGTENRQIFDVMLSTVSNRVGSNEQTVTFDHQKPTGHYPNTYGTTSLRLPVGEGKIDLQ

SQLLFGTVTNQGTLINSEADYKAYQEQLIAGRRFVDPGYAYKNFAVTYDAYKVRVTDSTL

GVTDEKKLSTSKEETYKVEFFSPTNGTKPVHEAKVVVGAEKTMMVNLAAGATVIKSDSHE

NAKKVFDGAIEYNPLSFSSKISITFEFKEPGLVKYWRFFNDITRKDDYIKEAKLEAFVGH

LEDDSKVKDSLEKSTEWVTVSDYSGEAQEFSQPLDNISAKYWRVTVDTKGGRYSSPSLPE

LQILGYRLPLTHDYKDDDDK

Endo S Nucleotide Sequence (SEQ ID NO: 12; codon optimized)
atgagagtgcctgctcagctgctgggcctgctgctgctgtggctgcctggtgctagatgc gcccagcacgactccctgatcagagtgaaggccgaggacaaggtggtgcagacctccct tccgtgtccgccatcgacgacctgcactacctgtccgagaactccaagaaagagttcaaa gagggcctgtccaaggccggcgaggtgcccgaaaagctgaaggacatcctgagcaaggct cagcaggccgacaagcaggccaaggtgctggccgagatgaaggtgccagagaagatcgcc atgaagcccctgaagggccctctgtacggcggctacttcagaacctggcacgacaagacc tccgaccccgccgagaaggacaaagtgaactccatgggcgagctgcccaaagaggtggac ctggccttcgtgttccacgactggaccaaggactactccctgttctggcaggaactggcc accaagcacgtgcccaccctgaacaagcagggcaccagagtgatccggacaatcccctgg cggtttctggctggcggcgaccactctggaatcgccgaggataccagaagtaccccaac acccccgagggcaacaaggccctggctaaggccatcgtggacgagtacgtgtacaagtac aacctggacggcctggacgtggacatcgagcgggactccatccctaaagtgaacggcaaa gagtccaacgagaacatccagcggtctatcgccgtgttcgaggaaatcggcaagctgatc ggccccaagggcgccgacaagtcccggctgttcatcatggactccacctacatggccgat aagaaccccctgatcgagagaggcgccccttacatcgatctgctgctggtgcaggtgtac ggcatccagggcgagaagggcgattgggaccctgtggcccggaagcctgaaaagaccatg gaagagatgggagtcctactccaagtacatccggcccgagcagtatatggtgggattc agcttctacgaggaaacgccggctccggcaacctgtggtacgacatcaacgagcggaag gacgaccacaaccctctgaactccgagatcgccggcacccgggctgagagatacgctaag tggcagcccaagaccggcggagtgaagggcggcatcttctcctacgccatcgataggat
```

-continued

```
ggcgtggcccaccagcctaagaaggtgtccgacgacgagaagcggaccaacaaggctatc aaggacatcaccgacggcatcgtgaagtccgactacaaggtgtccaaagccctgaagaaa gtgatggaaaacgacaagagctacgagctgatcgaccagaaggacttccccgataaggcc ctgcgcgaggccgtgattgctcaagtgggctccagacggggcgacctggaaagattcaac ggcaccctgcggctggacaaccccgacatcaagtccctggaaggcctgaacaaactgaag aagctggccaagctggaactgatcggactgtcccagatcacaaagctggactcctccgtg ctgcctgagaacatcaagcccaccaaggacaccctggtgtccgtgctggaaacctacaag aacgacgaccggaaagaggaagccaaggccatccctcaggtggccctgaccatctctggc ctgaccggcctgaaagagctgaatctggccggcttcgacgggattccctggctggaatc gatgccgctctctgacctccctggaaaaagtggacctgtctaagaacaagctggatctg gctgccggcaccgagaaccggcagatcttcgacgtgatgctgtccaccgtgtccaacaga gtgggcagcaacgagcagaccgtgaccttcgaccaccagaagcccaccggccactaccct aacacctacggcaccacctccctgagactgcctgtgggcgagggcaagatcgacctgcag tcccagctgctgttcggcaccgtgaccaaccagggcacactgatcaactccgaggccgat tacaaggcctaccaggaacagctgatcgctgggcggagattcgtggaccctggctacgct tacaagaacttcgccgtgacctacgatgcctacaaagtgcgcgtgaccgactccaccctg ggcgtgacagacgaaaagaagctgagcacctccaaagaagagacataccaggtggaattc ttctcccccaccaatggcaccaagcctgtgcatgaggctaaggtggtcgtgggcgccgag aaaaccatgatggtcaacctggccgctggcgccaccgtgatcaagtctgactctcacgag aatgccaaaaggtgttcgacggcgccatcgagtacaatcctctgagcttctccagcaag accagcatcaccttcgagtttaaagaacccggcctcgtgaaatactggcggttcttcaac gatatcacccgcaaggacgactacatcaaagaggctaagctggaagccttcgtgggccat ctggaagatgactccaaagtgaaggactctctggaaaagtccaccgagtgggtcaccgtg tctgactactctggcgaggcccaggaattctcccagcccctggacaacatctccgccaag tattggagagtgaccgtggacaccaagggcggacggtacagctctcctagcctgcccgag ctgcagatcctgggctacagactgcctctgacccacgactataaggacgacgacgacaaa tga
```

In some embodiments, an Endo S enzyme described herein can be an enzyme (e.g., a wild-type enzyme) that share at least 85% (e.g., 90%, 93%, 95%, 96%, 97%, 98%, or 99%) sequence identity as compared with SEQ ID NO:11. Examples include, but are not limited to, those described under GenBank Accession Nos. EQB24254.1, WP_037584019.1, WP_012679043.1, and ADC53484.1.

C. Genetically Engineered Host Animal Cells

The host animal cells described herein are genetically engineered to overly express one or more enzymes having specific glycan-modifying activities (e.g., glycosidase or glycol-transferase). A genetically engineered host animal cell is an animal cell that carry exogenous (non-native) genetic materials, such as exogenous genes encoding one or more of the fucosidase and endoglycosidase described herein. A host cell that overly expresses an enzyme refers to a genetically engineered host cell that expresses the enzyme in a level greater (e.g., 20%, 50%, 80%, 100%, 2-fold, 5-fold, 10-fold, 50-fold, 100-fold, 1,000-fold, $10^4$-fold, or $10^5$-fold higher) than that of the enzyme in the wild-type counterpart of the host cell, i.e., the same type of cell that does not contain the same genetic modification as the genetically engineered host cell. In some embodiments, a gene encoding an exogenous enzyme as described herein can be introduced into a suitable parent animal cell to produce the genetically engineered host animal cell described herein. An exogenous enzyme refers to an enzyme that does not exist in the parent cell used for making the engineered host animal cell.

Genetically engineered host animal cells as described herein, which are capable of producing glycoproteins having modified glycosylation as compared with the wild-type counterpart, can be prepared by the routine recombinant technology. In some instances, a strong promoter can be inserted upstream to an endogenous fucosidase and/or endoglycosidase gene to enhance its expression. In other instances, exogenous genetic materials encoding one or more fucosidases and/or endoglycosidases can be introduced into a parent host cell to produce the genetically engineered host animal cells as described herein.

A gene encoding a fucosidase or endoglycosidase as described herein can be inserted into a suitable expression vector (e.g., a viral vector or a non-viral vector) using methods well known in the art. Sambrook et al., Molecular Cloning, A Laboratory Manual, 3rd Ed., Cold Spring Harbor Laboratory Press. For example, the gene and the vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. In some embodiments, the gene of the fucosidase or endoglycosidase is contained in an expression cassette comprising one of more of the following elements: a Kozak sequence and a signal peptide sequence, which are located at the N-terminus of the enzyme, and a protein tag (e.g., FLAG, His-tag, include chitin binding protein (CBP), maltose binding protein (MBP), and glutathione-S-transferase (GST)). The protein tag can be located at either the N-terminus or C-terminus of the enzyme. See, e.g., FIG. 2, panel B.

Additionally, the expression vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Suitable vectors and methods for producing vectors containing transgenes are well known and available in the art. Sambrook et al., Molecular Cloning, A Laboratory Manual, 3rd Ed., Cold Spring Harbor Laboratory Press.

If two or more enzymes are to be used in constructing the host animal cells described herein, for example, two or more fucosidases, two or more endoglycosidases, or a combination of fucosidase and endoglycosidase, genes encoding the two or more enzymes can be inserted into separate express vectors or inserted into a common express vector designed for producing multiple proteins.

Expression vectors for producing the fucosidase and/or endoglycosidase may be introduced into suitable parent host cells, including, but are not limited to, murine myeloma cells (e.g., NSO cells), Chinese Hamster Ovary (CHO) cells, human embryonic kidney cells (e.g., HEK293), and human retinoblastoma cells (e.g., PER.C6). Selection of a suitable host cell line, which is within the knowledge of those skilled in the art, would depend on the balance between the need for high productivity and the need for producing the product having desired properties. In some instances, the expression vectors can be designed such that they can incorporate into the genome of cells by homologous or non-homologous recombination by methods known in the art. Methods for transferring expression vectors into the parent host cells include, but are not limited to, viral mediated gene transfer, liposome mediated transfer, transformation, transfection and transduction, e.g., viral mediated gene transfer such as the use of vectors based on DNA viruses such as adenovirus, adeno-associated virus and herpes virus, as well as retroviral based vectors. Examples of modes of gene transfer include e.g., naked DNA, $CaPO_4$ precipitation, DEAE dextran, electroporation, protoplast fusion, lipofection, cell microinjection, and viral vectors, adjuvant-assisted DNA, gene gun, catheters. In one example, a viral vector is used. To enhance delivery of non-viral vectors to a cell, the nucleic acid or protein can be conjugated to antibodies or binding fragments thereof which bind cell surface antigens. Liposomes that also include a targeting antibody or fragment thereof can be used in the methods described herein.

A "viral vector" as described herein refers to a recombinantly produced virus or viral particle that comprises a polynucleotide to be delivered into a host cell, either in vivo, ex vivo or in vitro. Examples of viral vectors include retroviral vectors such as lentiviral vectors, adenovirus vectors, adeno-associated virus vectors and the like. In aspects where gene transfer is mediated by a retroviral vector, a vector construct refers to the polynucleotide comprising the retroviral genome or part thereof, and a therapeutic gene.

The genetically engineered animal host cells can comprise the use of an expression cassette created for either constitutive or inducible expression of the introduced gene(s). Such an expression cassette can include regulatory elements such as a promoter, an initiation codon, a stop codon, and a polyadenylation signal. The elements can be operably linked to the gene encoding the surface protein of interest such that the gene is operational (e.g., is expressed) in the host cells.

A variety of promoters can be used for expression of the fucosidase and/or endoglycosidase (as well as any exogenous glycoproteins as described herein). Promoters that can be used to express the protein are well known in the art, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, E. coli lac UV5 promoter and the herpes simplex tk virus promoter.

Regulatable promoters can also be used. Such regulatable promoters include those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone or rapamycin. Inducible systems are available from Invitrogen, Clontech and Ariad.

The effectiveness of some inducible promoters can be increased over time. In such cases one can enhance the effectiveness of such systems by inserting multiple repressors in tandem, e.g., TetR linked to a TetR by an internal ribosome entry site (IRES). Alternatively, one can wait at least 3 days before screening for the desired function. While some silencing may occur, it can be minimized by using a suitable number of cells, preferably at least $1 \times 10^4$, more preferably at least $1 \times 10^5$, still more preferably at least $1 \times 10^6$, and even more preferably at least $1 \times 10^7$. One can enhance expression of desired proteins by known means to enhance the effectiveness of this system. For example, using the Woodchuck Hepatitis Virus Posttranscriptional Regulatory Element (WPRE). See Loeb, V. E., et al., Human Gene Therapy 10:2295-2305 (1999); Zufferey, R., et al., J. of Virol. 73:2886-2892 (1999); Donello, J. E., et al., J. of Virol. 72:5085-5092 (1998).

Examples of polyadenylation signals useful to practice the methods described herein include, but are not limited to, human collagen I polyadenylation signal, human collagen II polyadenylation signal, and SV40 polyadenylation signal.

The exogenous genetic material that includes fucosidase gene and/or endoglycosidase gene (as well as a glycoprotein gene as described herein) operably linked to the regulatory elements may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA, which can integrate into the chromosome, may be introduced into the cell. When introducing DNA into the cell, reagents, which promote DNA integration into chromosomes, may be added. DNA sequences, which are useful to promote integration, may also be included in the DNA molecule. Alternatively, RNA may be introduced into the cell.

Selectable markers can be used to monitor uptake of the desired transgene into the host animal cells described herein. These marker genes can be under the control of any promoter or an inducible promoter. These are known in the art and include genes that change the sensitivity of a cell to a stimulus such as a nutrient, an antibiotic, etc. Genes include those for neo, puro, tk, multiple drug resistance (MDR), etc. Other genes express proteins that can readily be screened for such as green fluorescent protein (GFP), blue fluorescent protein (BFP), luciferase, and LacZ.

D. Producing Glycoproteins Having Modified Glycosylation

The genetically engineered host animal cells can be used for producing glycoproteins (e.g., endogenous or exogenous) having modified glycosylation patterns. In some embodiments, the parent host cell for use to producing the engineered host animal cells described above already carries a gene(s) encoding an exogenous glycoprotein. In other embodiments, a gene or multiple genes encoding a glycoprotein of interest can be introduced into the genetically engineered host animal cells that express one or more fucosidase and/or endoglycosidase by methods known in the art or described herein.

Genetically engineered host animal cells capable of producing both a glycoprotein of interest and one or more of fucosidases and/or endoglycosidases can be cultured under suitable conditions allowing for expression of these proteins. The cells and/or the culture medium can be collected and the glycoprotein of interested can be isolated and purified from the cells and/or the culture medium by routine technology. The glycosylation pattern of the glycoprotein thus produced can be determined by routine technology, e.g., LC/MS/MS, to confirm modification of glycosylation.

In some examples, the glycoprotein of interest is an antibody. Exemplary antibodies include, but are not limited to, abciximab (glycoprotein IIb/IIIa; cardiovascular disease), adalimumab (TNF-α, various auto-immune disorders, e.g., rheumatoid arthritis), alemtuzumab (CD52; chronic lymphocytic leukemia), basiliximab (IL-2Rα receptor (CD25); transplant rejection), bevacizumab (vascular endothelial growth factor A; various cancers, e.g., colorectal cancer, non-small cell lung cancer, glioblastoma, kidney cancer; wet age-related macular degeneration), catumaxomab, cetuximab (EGF receptor, various cancers, e.g., colorectal cancer, head and neck cancer), certolizumab (e.g., certolizumab pegol) (TNF alpha; Crohn's disease, rheumatoid arthritis), Daclizumab (IL-2Rα receptor (CD25); transplant rejection), eculizumab (complement protein C5; paroxysmal nocturnal hemoglobinuria), efalizumab (CD11a; psoriasis), gemtuzumab (CD33; acute myelogenous leukemia (e.g., with calicheamicin)), ibritumomab tiuxetan (CD20; Non-Hodgkin lymphoma (e.g., with yttrium-90 or indium-111)), infliximab (TNF alpha; various autoimmune disorders, e.g., rheumatoid arthritis) Muromonab-CD3 (T Cell CD3 receptor; transplant rejection), natalizumab (alpha-4 (α4) integrin; multiple sclerosis, Crohn's disease), omalizumab (IgE; allergy-related asthma), palivizumab (epitope of RSV F protein; Respiratory Syncytial Virus infection), panitumumab (EGF receptor; cancer, e.g., colorectal cancer), ranibizumab (vascular endothelial growth factor A; wet age-related macular degeneration), rituximab (CD20; Non-Hodgkin lymphoma), tositumomab (CD20; Non-Hodgkin lymphoma), trastuzumab (ErbB2; breast cancer).

In some examples, the glycoprotein of interest is a cytokine. Examples include, but are not limited to, interferons (e.g., IFN-α, INF-β, or INF-γ), interleukins (e.g., IL-2, IL-3, IL-4, IL-5, IL-6, IL-7, IL-12), and colony stimulating factors (e.g., G-CSF, GM-CSF, M-CSF). The IFN can be, e.g., interferon alpha 2a or interferon alpha 2b. See, e.g., Mott H R and Campbell I D. "*Four-helix bundle growth factors and their receptors: protein-protein interactions.*" Curr Opin Struct Biol. 1995 February; 5(1):114-21; Chaiken I M, Williams W V. "*Identifying structure-function relationships in four-helix bundle cytokines: towards de novo mimetics design.*" Trends Biotechnol. 1996 October; 14(10):369-75; Klaus W, et al., "*The three-dimensional high resolution structure of human interferon alpha-2a determined by heteronuclear NMR spectroscopy in solution*". J. Mol Biol., 274(4):661-75, 1997, for further discussion of certain of these cytokines.

The protein of interest may also be a cytokine protein that has a similar structure to one or more of the afore-mentioned cytokines. For example, the cytokine can be an IL-6 class cytokine such as leukemia inhibitory factor (LIF) or oncostatin M. In some embodiments, the cytokine is one that in nature binds to a receptor that comprises a GP130 signal transducing subunit. Other four-helix bundle proteins of interest include growth hormone (GH), prolactin (PRL), and placental lactogen. In some embodiments, the target protein is an erythropoiesis stimulating agent, e.g., (EPO), which is also a four-helix bundle cytokine. In some embodiments, an erythropoiesis stimulating agent is an EPO variant, e.g., darbepoetin alfa, also termed novel erythropoiesis stimulating protein (NESP), which is engineered to contain five N-linked carbohydrate chains (two more than recombinant HuEPO). In some embodiments, the protein comprises five helices. For example, the protein can be an interferon beta, e.g., interferon beta-1a or interferon beta-1b, which (as will be appreciated) is often classified as a four-helix bundle cytokine. In some embodiments, a target protein is IL-9, IL-10, IL-11, IL-13, or IL-15. See, e.g., Hunter, C A, Nature Reviews Immunology 5, 521-531, 2005, for discussion of certain cytokines. See also Paul, W E (ed.), Fundamental Immunology, Lippincott Williams & Wilkins; 6th ed., 2008.

In addition, the protein of interest may be a protein that is approved by the US Food & Drug Administration (or an equivalent regulatory authority such as the European Medicines Evaluation Agency) for use in treating a disease or disorder in humans. Such proteins may or may not be one for which a PEGylated version has been tested in clinical trials and/or has been approved for marketing. In some instances, the protein of interest is an Fc-fusion protein, including, but not limited to, abatacept, entanercept, IL-2-Fc fusion protein, CD80-Fc fusion protein, and PDL1-Fc fusion protein.

Further, the protein of interest may be a neurotrophic factor, i.e., a factor that promotes survival, development and/or function of neural lineage cells (which term as used herein includes neural progenitor cells, neurons, and glial cells, e.g., astrocytes, oligodendrocytes, microglia). For example, in some embodiments, the target protein is a factor that promotes neurite outgrowth. In some embodiments, the protein is ciliary neurotrophic factor (CNTF; a four-helix bundle protein) or an analog thereof such as Axokine, which is a modified version of human Ciliary neurotrophic factor with a 15 amino acid truncation of the C terminus and two amino acid substitutions, which is three to five times more potent than CNTF in in vitro and in vivo assays and has improved stability properties.

Alternatively, the protein of interest can be an enzyme, e.g., an enzyme that is important in metabolism or other physiological processes. As is known in the art, deficiencies of enzymes or other proteins can lead to a variety of disease. Such diseases include diseases associated with defects in carbohydrate metabolism, amino acid metabolism, organic acid metabolism, porphyrin metabolism, purine or pyrimidine metabolism, lysosomal storage disorders, blood clotting, etc. Examples include Fabry disease, Gaucher disease, Pompe disease, adenosine deaminase deficiency, asparaginase deficiency, porphyria, hemophilia, and hereditary angioedema. In some embodiments, a protein is a clotting or coagulation factor, (e.g., factor VII, VIIa, VIII or IX). In other embodiments a protein is an enzyme that plays a role in carbohydrate metabolism, amino acid metabolism, organic acid metabolism, porphyrin metabolism, purine or pyrimidine metabolism, and/or lysosomal storage, wherein exogenous administration of the enzyme at least in part alleviates the disease.

Further, the protein of interest can be a hormone, such as insulin, growth hormone, Luteinizing hormone, follicle-stimulating hormone, and thyroid-stimulating hormone. The protein of interest can also be a growth factor, including, but not limited to, adrenomedullin (AM), angiopoietin (Ang), autocrine motility factor, bone morphogenetic proteins (BMPs), brain-derived neurotrophic factor (BDNF), epidermal growth factor (EGF), erythropoietin (EPO) fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), healing factor, hepatocyte growth factor (HGF) hepatoma-derived growth factor (HDGF), insulin-like growth factor (IGF), keratinocyte growth factor (KGF), migration-stimulating factor (MSF), myostatin (GDF-8), nerve growth factor (NGF) and other neurotrophins, platelet-derived growth factor (PDGF), thrombopoietin (TPO), transforming growth factor alpha(TGF-α), transforming growth factor beta(TGF-β), tumor necrosis factor-alpha(TNF-α), vascular endothelial growth factor (VEGF), and placental growth factor (PGF).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Examples

Methods
i. Construction of Expression Vectors for Producing a Fucosidase or an Endoglycosidase.

Figure 2:
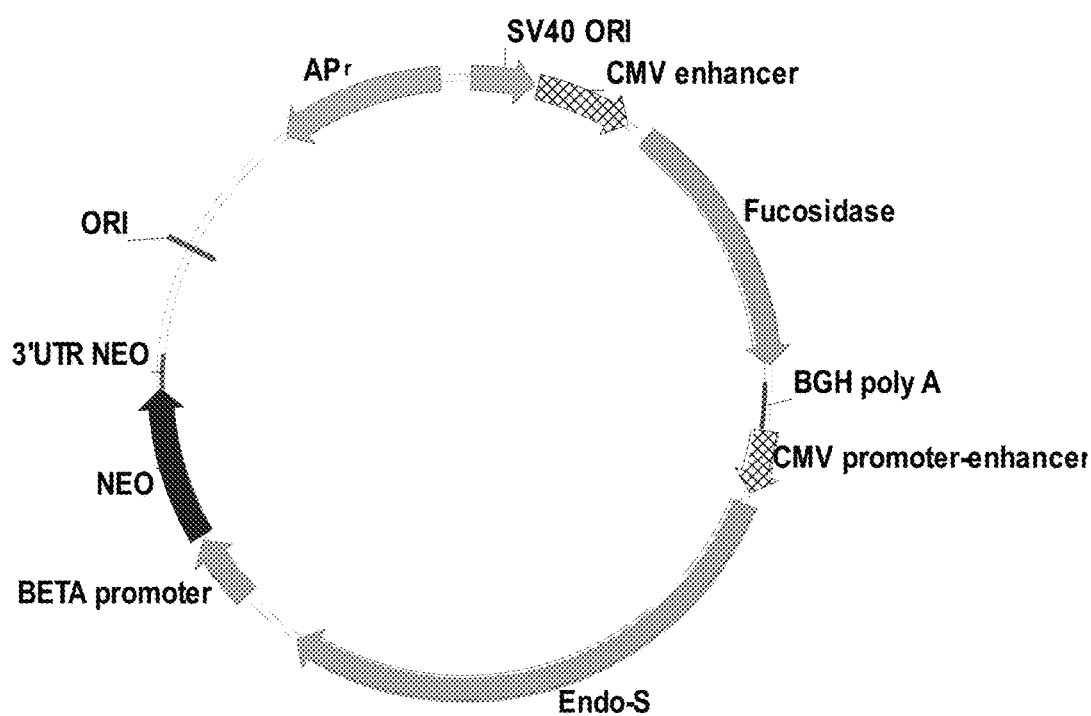
FIG. 2 is a schematic illustration of an exemplary expression vector for producing a fucosidase. A: map of an exemplary plasmid that carries a fucosidase gene. B: an exemplary expression cassette for expressing a fucosidase or an endoglycosidase S.

In order to construct expression vectors for a fucosidase or an endoglycosidase, fucosidase or endoglycosidase gene was isolated by routine technology and subjected to codon optimization based on codon usage of hamster cells. The synthetic genes were prepared by GeneArt Corp. and cloned into pcDNA3.1 B(−) Myc-His vector (Invitrogen, US) at restriction sites Bgl II/EcoR I. (FIG. 2, panel A). The expression cassette of an alpha-fucosidase comprises, from 5' to 3', a Kozak sequence, an Igk leader sequence, the coding sequence of the fucosidase, and a sequence encoding a His-tag. FIG. 2, panel B. The expression cassette of an endoglycosidase comprises, from 5' to 3', a Kozak sequence, an Igk leader sequence, the coding sequence of the endoglycosidase, and a sequence encoding a Flag tag. FIG. 2, panel B.

ii. Preparation of Defucosylated Antibody

An antibody producing cell line was maintained at $0.3~3.0\times10^6$ viable cells/mL in a complete medium, CD FortiCHO™ medium supplemented with 8 mM L-glutamine and anti-Clumping Agent at 1:100 dilution (Life Technologies, USA). Cells were maintained on a shaking platform setting at 130-150 rpm in an 8% $CO_2$ incubator.

To produce defucosylated antibodies, the antibody-producing cells noted above were transfected with the expression vector encoding an alpha-fucosidase described above by FreeStyleMAX reagent (Life Technologies, USA) according to manufacturer's protocol. Transfected cells were cultured in a medium comprising 4 g/L of glucose and the medium was changed every other day. The cells were harvested when the cell viability was dropped below 70% Clarified culture supernatant was collected and purified by Protein A Chromatography.

iii. Analysis of Glycosylation of Antibodies

Recombinant antibodies prepared according to the methods described herein were reduced, alkylated, and digested overnight with trypsin in the presence of 25 mM ammonium bicarbonate buffer (pH~8) at 37° C. PNGase F solution (3 μL, Roche) was added to 200 μL of the digested sample and the mixture was incubated for another 16 hours at 37° C. The released glycans were separated from the peptides using a Sep-Pak® C18 cartridge (Waters). The Sep-Pak C18 was washed with acetonitrile, followed by water. The PNGaseF digested sample was loaded onto the cartridge and the released glycans were eluted with 1% ethanol while the peptides remained bound to the Sep-Pak C18. The released protein oligosaccharides were first purified using a porous graphite carbon column (PhyNexus) and then permethylated. All mass spectrometry experiments were performed using an Orbitrap Fusion Tribrid mass spectrometer via direct infusion into the nano-electrospray source.

Results

1. Production of Antibodies h4B12, Rituximab, and Omalizumab Having Mono-Sugar (GlcNAc) Glycoform A monosaccharide glycovariant could be made from the aforementioned di-sugar variant by a fucosidase cleavage reaction. Search from a number of available enzymes and glycol-peptide analysis by LC/MS/MS indicated that, with optimized cleavage reaction conditions, an efficient de-fucosidation could be achieved using an α-1,6-fucosidase, and that a higher cleavage efficiency is associated with a lower NF/N ratio. Alternatively, a mono-sugar glycovariant could be obtained with two reaction enzymes combined in sequence, including an endoglycosisase (Endo S) and an α-1,6-fucosidase. The resultant mono-GlcNAc glycovariant was shown in FIG. 3, panel A.

Figure 3:
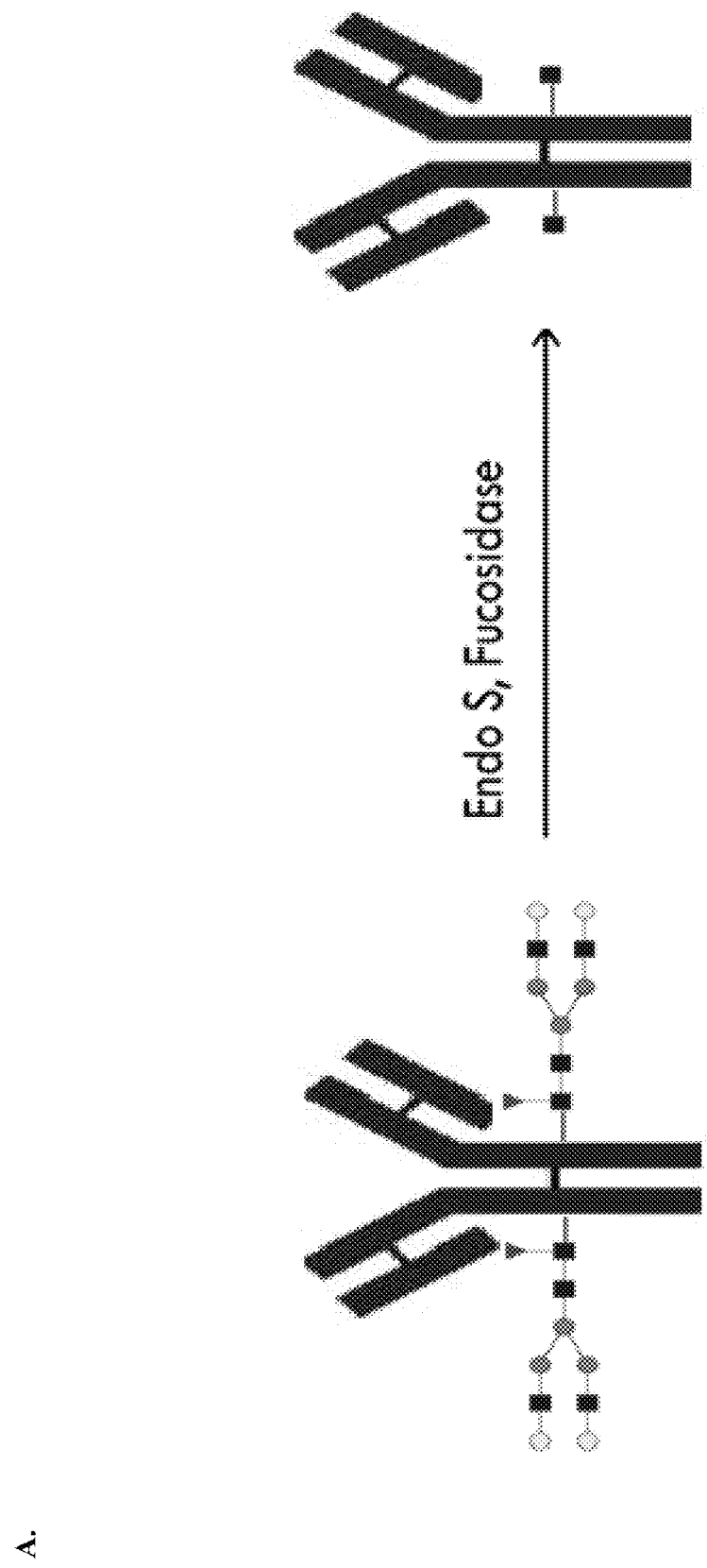
FIG. 3 includes diagrams showing the production of homogenous afucosylated mono-sugar (GlcNAc) antibody h4B12 by transient expression of the antibody in host cells engineered to express a fucosidase and/or an endoglycosidase. A: a schematic illustration of producing homogenous afucosylated mono-sugar (GlcNAc) antibodies. B: a chart showing the glycosylation of antibody 4B12 produced in host cells engineered to express human FUCA1, human FUCA2, *C. griseus* fucosidase, alpha-L-1, or *C. meningosepticum* α1,6-fucosidase, as determined by LC/MS/MS. C: a diagram showing the transient expression of a fucosidase or an endoglycosidase as indicated in CHO cells detected by Western blot. D: a chart showing antibody h4B12 produced in CHO cells expressing a fucodisase or an endoglycosidase as indicated, the antibody having homogenous fucose-free mono-sugar (GlcNAc) glycoform as determined by LC/MS/MS. A homogenous N-glycan refers to the ratio of that N-glycan (e.g., an afucosylated N-glycan) to the total N-glycans in a glycoprotein such as an antibody.
Figure 3:
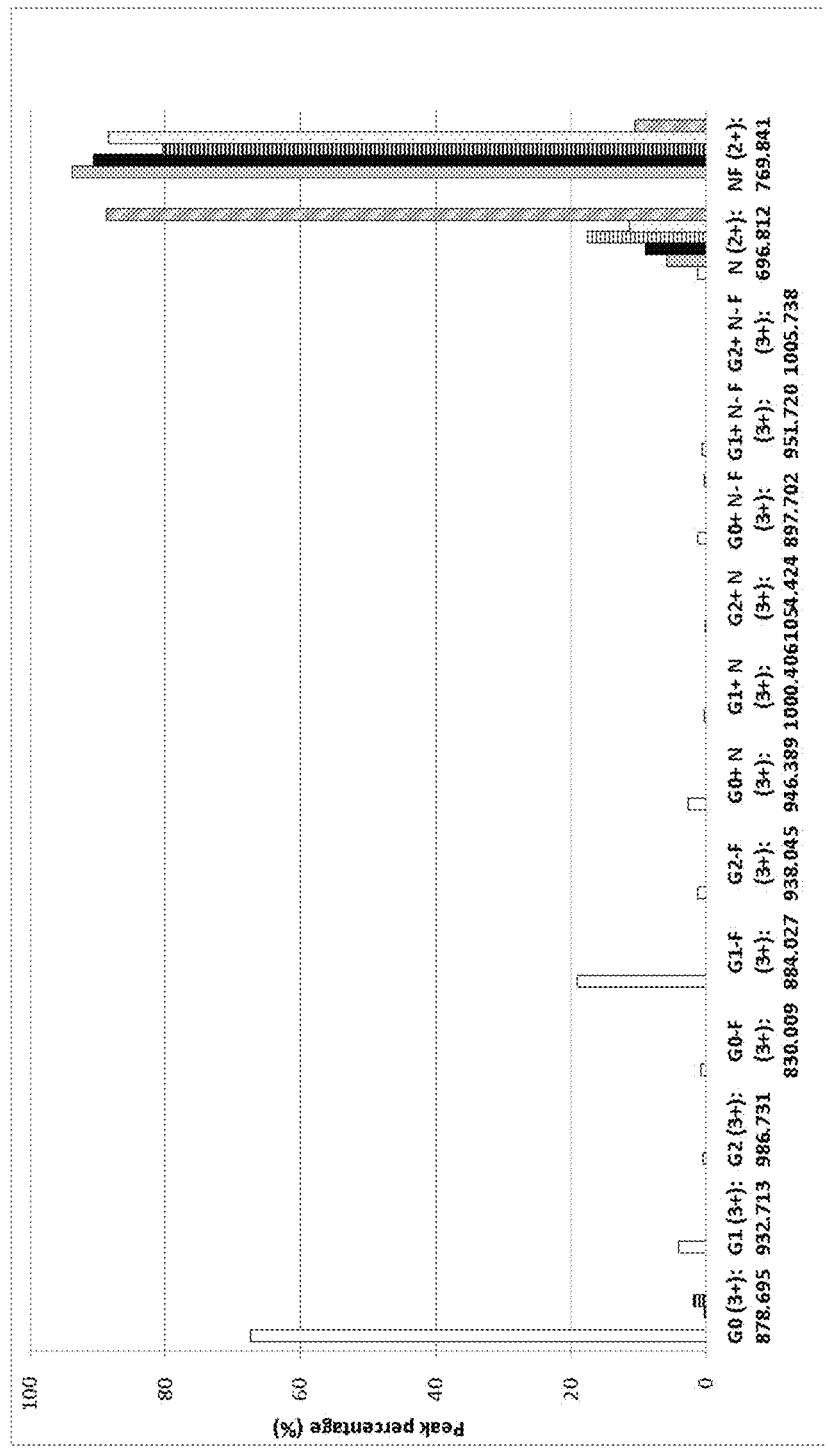
Figure 3:
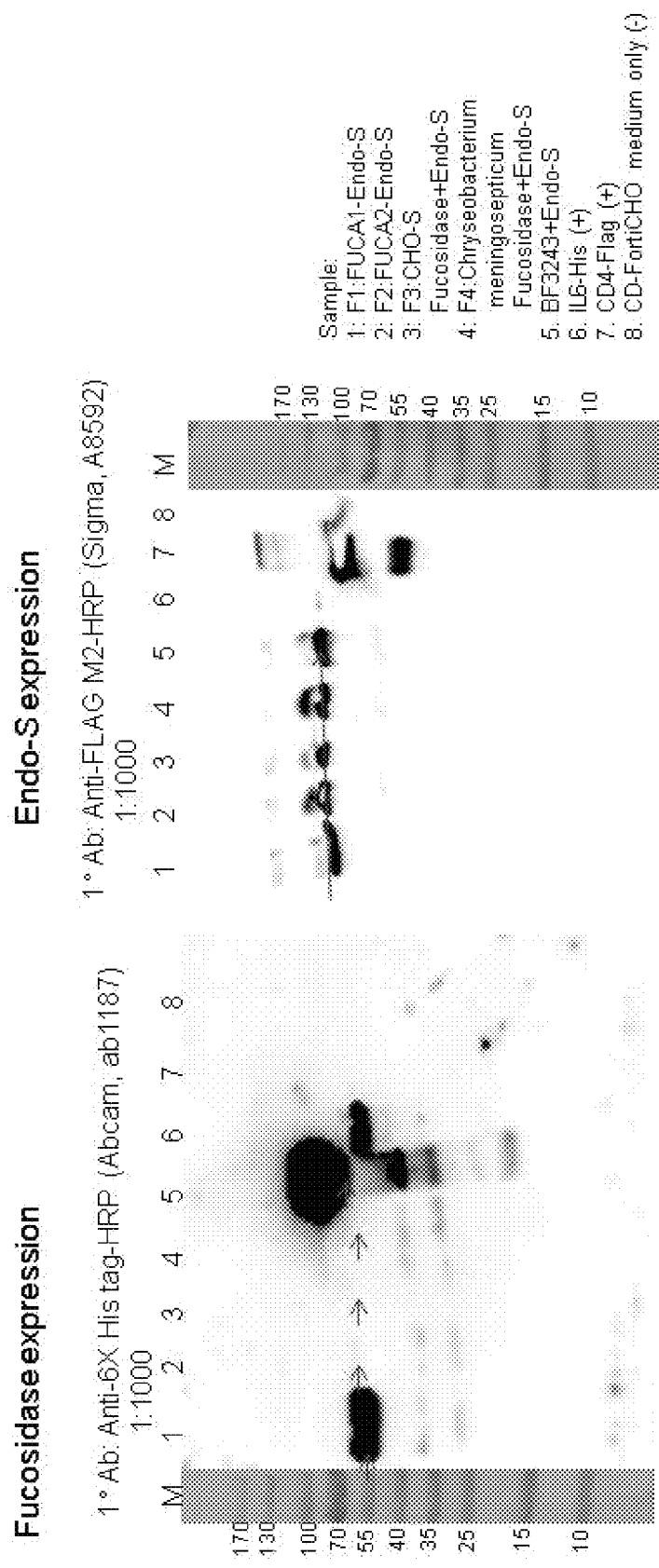
Figure 3:
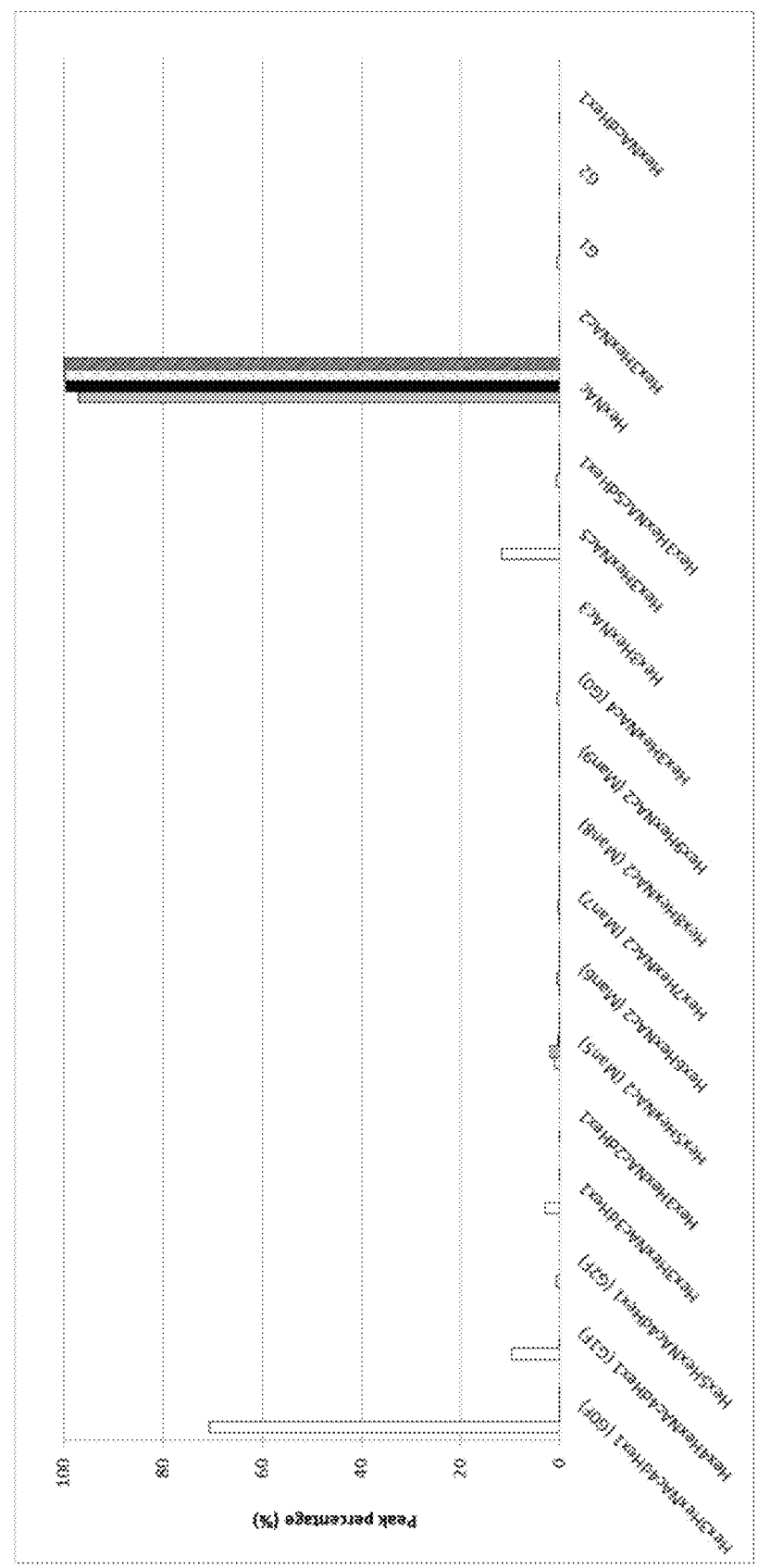

The results show that Endo-S removed >90% N-linked glycans of the heavy chain of h4B12, rituximab, and omalizumab produced in the engineered CHO cells described herein. The defucosylation ability of five different types of fucosidases: FUCA1, FUCA2, Cricetulus griseus fucosidase, alpha-L-1, Chryseobacterium meningosepticum α1,6-Fucosidas, and BF3242 are 5.8%, 9.1%, 17.7%, 11.5 and 68%, respectively, in relation to h4B12 antibodies produced in the CHO cells expressing each of the fucosidase. FIG. 3, panel B. The expression of the enzymes was detect by Western blot as shown in FIG. 3, panel C.

2-deoxy-2-fluoro L-Fucose is a fluorinated fucose analog. It can be metabolized inside host cells to generate a substrate-based inhibitor of fucosyltransferases. When culturing antibody-producing CHO cells transiently expressing fucosidase BF3242 and Endo-S, 99.89% of the N-glycans linked to the antibody produced in the CHO cells are monoglycosylated (GlcNAc-Ig-Fc). FIG. 3, panel D.

Figure 4:
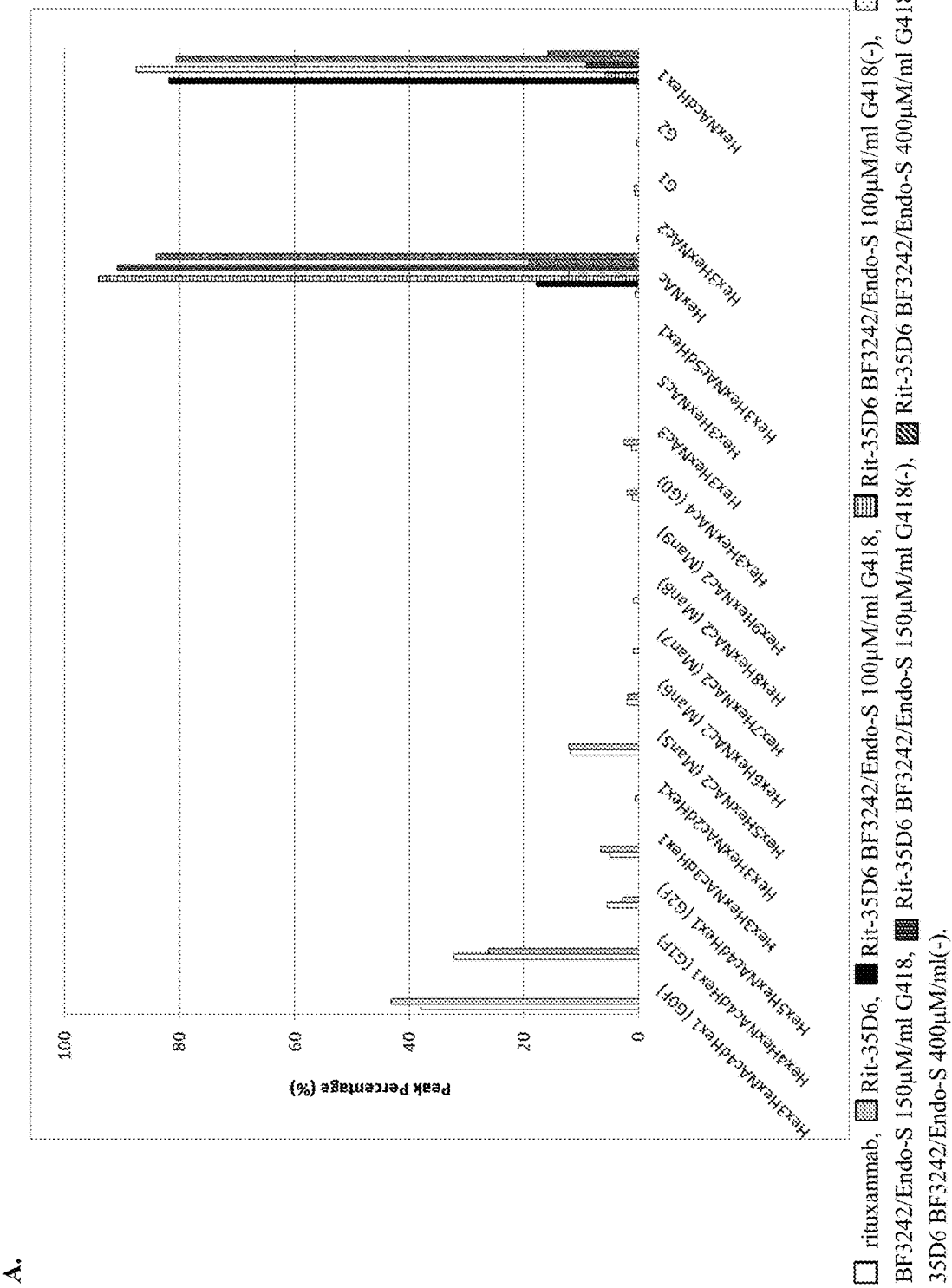
FIG. 4 includes diagrams showing the production of homogenous afucosylated mono-sugar (GlcNAc) antibody rituximab by transient expression of the antibody in host cells engineered to express a fucosidase and/or an endoglycosidase. A: a chart showing the glycosylation of antibody rituximab produced in host cells engineered to express various fucosidases or endoglycosidases as indicated. B: a diagram showing the transient expression of a fucosidase (left lane) or an endoglycosidase (right lane) as indicated in CHO cells as detected by Westernblot.
Figure 4:
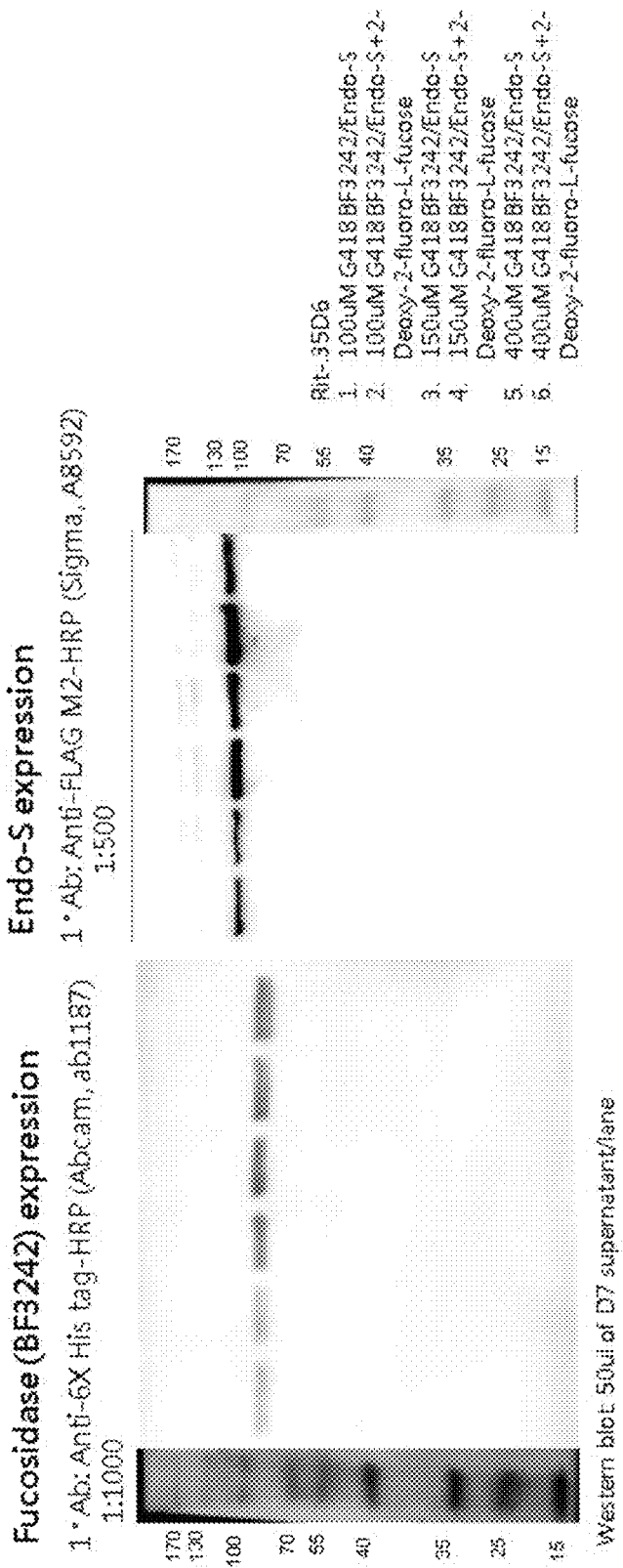

CHO-35D6 cells, which produce rituximab, were stable transfected with an expression vector for producing BF3242 and Endo-S. The cells were cultured in the presence of 100~400 µg/ml G418. The antibody thus produced contains 17-19% of GlcNAc-Ig-Fc. FIG. 4, panel A. Enzyme expression was detect by Western blot as shown in FIG. 4, panel B.

Similar results were observed in omalizumab produced in CHO cells engineered to express both a fucosidase and Endo S.

Such efficiency represents an important step for transglycosylation in the preparation of antibodies with homogeneous glycan form.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

---

What is claimed is:

1. A genetically engineered host animal cell, which expresses an exogenous fucosidase, and an exogenous endoglycosidase, wherein the engineered host animal cell produces glycoproteins having modified glycosylation, and wherein the endoglycosidase is a bacterial enzyme.

2. The genetically engineered host animal cell of claim 1, wherein the fucosidase is a mammalian fucosidase or a bacterial fucosidase.

3. The genetically engineered host animal cell of claim 1, wherein the endoglycosidase is an Endo S enzyme, an endoglycosidase D enzyme, an endoglycosidase F enzyme, an endoglycosidase F1 enzyme, an endoglycosidase F2 enzyme, or an endoglycosidase H enzyme.

4. The genetically engineered host animal cell of claim 1, which further expresses a glycoprotein.

5. The genetically engineered host animal cell of claim 4, wherein the glycoprotein is exogenous.

6. The genetically engineered host animal cell of claim 5, wherein the glycoprotein is an antibody, an Fc-fusion protein, a cytokine, a hormone, a growth factor, or an enzyme.

7. The genetically engineered host animal cell of claim 6, wherein the glycoprotein is an antibody.

8. The genetically engineered host animal cell of claim 1, wherein the animal cell is a mammalian cell.

9. The genetically engineered host animal cell of claim 8, wherein the mammalian cell is a Chinese hamster ovary (CHO) cell, a rat myeloma cell, a baby hamster kidney (BHK) cell, a hybridoma cell, or a Namalwa cell.

10. The genetically engineered host animal cell of claim 1, which expresses (i) human FUCA1, human FUCA2, *Cricetulus griseus* fucosidase, alpha-L-1 *Chryseobacterium meningosepticum* □1,6-fucosidase, or bacterial fucosidase BF3242, and (ii) an Endo S.

11. A method for producing a defucosylated glycoprotein, comprising:
providing a genetically engineered host animal cell expressing (a) a glycoprotein, and (b) an exogenous fucosidase, and an exogenous endoglycosidase, wherein the endoglycosidase is a bacterial enzyme;
culturing the host animal cell under conditions allowing for producing the glycoprotein and the fucosidase, the endoglycosidase, or both; and
collecting the host animal cell or the culture supernatant for isolating the glycoprotein.

12. The method of claim 11, wherein the fucosidase is a mammalian fucosidase or a bacterial fucosidase.

13. The method of claim 11, wherein the endoglycosidase is an Endo S enzyme.

14. The method of claim 11, wherein the glycoprotein is exogenous.

15. The method of claim 11, wherein the glycoprotein is an antibody, an Fc-fusion protein, a cytokine, a hormone, a growth factor, or an enzyme.

16. The method of claim 15, wherein the glycoprotein is an antibody.

17. The method of claim 11, wherein the genetically engineered host animal cell is a mammalian cell.

18. The method of claim 17, wherein the mammalian cell is a Chinese hamster ovary (CHO) cell, a rat myeloma cell, a baby hamster kidney (BHK) cell, a hybridoma cell, or a Namalwa cell.

19. The method of claim 11, further comprising isolating the glycoprotein.

20. The method of claim 19, further comprising analyzing the glycosylation pattern of the glycoprotein.

21. A method for preparing the genetically engineered host animal cell of claim 1, comprising introducing into an animal cell one or more expression vectors, which collectively encode the exogenous fucosidase, and the exogenous endoglycosidase.

22. The method of claim 21, further comprising introducing into the animal cell an expression vector encoding a glycoprotein.

23. The genetically engineered host animal cell of claim 1, wherein the endoglycosidase is an Endo S enzyme.

* * * * *

SEQUENCE LISTING

```
<160> NUMBER OF SEQ ID NOS: 12

<210> SEQ ID NO 1
<211> LENGTH: 461
<212> TYPE: PRT
<213> ORGANISM: Artificial Sequence
<220> FEATURE:
<223> OTHER INFORMATION: Synthetic Polypeptide

<400> SEQUENCE: 1
```

Met Arg Val Pro Ala Gln Leu Leu Gly Leu Leu Leu Leu Trp Leu Pro
1               5                   10                  15

Gly Ala Arg Cys Gln Pro Pro Arg Arg Tyr Thr Pro Asp Trp Pro Ser
            20                  25                  30

Leu Asp Ser Arg Pro Leu Pro Ala Trp Phe Asp Glu Ala Lys Phe Gly
        35                  40                  45

Val Phe Ile His Trp Gly Val Phe Ser Val Pro Ala Trp Gly Ser Glu
    50                  55                  60

Trp Phe Trp Trp His Trp Gln Gly Glu Gly Arg Pro Gln Tyr Gln Arg
65                  70                  75                  80

Phe Met Arg Asp Asn Tyr Pro Pro Gly Phe Ser Tyr Ala Asp Phe Gly
                85                  90                  95

Pro Gln Phe Thr Ala Arg Phe Phe His Pro Glu Glu Trp Ala Asp Leu
            100                 105                 110

Phe Gln Ala Ala Gly Ala Lys Tyr Val Val Leu Thr Thr Lys His His
        115                 120                 125

Glu Gly Phe Thr Asn Trp Pro Ser Pro Val Ser Trp Asn Trp Asn Ser
    130                 135                 140

Lys Asp Val Gly Pro His Arg Asp Leu Val Gly Glu Leu Gly Thr Ala
145                 150                 155                 160

Leu Arg Lys Arg Asn Ile Arg Tyr Gly Leu Tyr His Ser Leu Leu Glu
                165                 170                 175

Trp Phe His Pro Leu Tyr Leu Leu Asp Lys Lys Asn Gly Phe Lys Thr
            180                 185                 190

Gln His Phe Val Ser Ala Lys Thr Met Pro Glu Leu Tyr Asp Leu Val
        195                 200                 205

Asn Ser Tyr Lys Pro Asp Leu Ile Trp Ser Asp Gly Glu Trp Glu Cys
    210                 215                 220

Pro Asp Thr Tyr Trp Asn Ser Thr Asn Phe Leu Ser Trp Leu Tyr Asn

```
                225                 230                 235                 240
Asp Ser Pro Val Lys Asp Glu Val Val Asn Asp Arg Trp Gly Gln
                245                 250                 255

Asn Cys Ser Cys His His Gly Gly Tyr Tyr Asn Cys Glu Asp Lys Phe
                260                 265                 270

Lys Pro Gln Ser Leu Pro Asp His Lys Trp Glu Met Cys Thr Ser Ile
                275                 280                 285

Asp Lys Phe Ser Trp Gly Tyr Arg Arg Asp Met Ala Leu Ser Asp Val
            290                 295                 300

Thr Glu Glu Ser Glu Ile Ile Ser Glu Leu Val Gln Thr Val Ser Leu
305                 310                 315                 320

Gly Gly Asn Tyr Leu Leu Asn Ile Gly Pro Thr Lys Asp Gly Leu Ile
                325                 330                 335

Val Pro Ile Phe Gln Glu Arg Leu Leu Ala Val Gly Lys Trp Leu Ser
                340                 345                 350

Ile Asn Gly Glu Ala Ile Tyr Ala Ser Lys Pro Trp Arg Val Gln Trp
                355                 360                 365

Glu Lys Asn Thr Thr Ser Val Trp Tyr Thr Ser Lys Gly Ser Ala Val
        370                 375                 380

Tyr Ala Ile Phe Leu His Trp Pro Glu Asn Gly Val Leu Asn Leu Glu
385                 390                 395                 400

Ser Pro Ile Thr Thr Ser Thr Thr Lys Ile Thr Met Leu Gly Ile Gln
                405                 410                 415

Gly Asp Leu Lys Trp Ser Thr Asp Pro Asp Lys Gly Leu Phe Ile Ser
                420                 425                 430

Leu Pro Gln Leu Pro Pro Ser Ala Val Pro Ala Glu Phe Ala Trp Thr
            435                 440                 445

Ile Lys Leu Thr Gly Val Lys His His His His His
            450                 455                 460

<210> SEQ ID NO 2
<211> LENGTH: 1386
<212> TYPE: DNA
<213> ORGANISM: Artificial Sequence
<220> FEATURE:
<223> OTHER INFORMATION: Synthetic Polynucleotide

<400> SEQUENCE: 2
atgagagtgc tgctcagct gctgggactg ctgctgctgt ggctgcctgg tgctagatgc        60
cagccccctc ggagatacac ccctgactgg ccttccctgg actccagacc tctgcccgct     120
tggtttgacg aggccaagtt cggcgtgttc atccactggg gcgtgttctc cgtgcctgcc     180
tggggctctg agtggttctg gtggcattgg cagggcgagg cagacctca gtaccagcgg      240 ttcatgcggg acaactaccc ccctggcttc tcctacgccg acttcggccc tcagttcacc     300
gcccggttct tccaccctga gaatgggcc gatctgttcc aggccgctgg cgccaaatac       360
gtggtgctga ccaccaagca ccacgagggc ttcaccaact ggccctcccc cgtgtcctgg     420
aactggaact ctaaggacgt gggcccccac cgggatctcg tgggagaact gggaaccgcc     480
ctgcggaagc ggaacatcag atacggcctg taccactccc tgctggaatg gttccacccc     540
ctgtacctgc tggacaagaa gaacggcttc aagacccagc acttcgtgtc cgccaagacc     600
atgcccgagc tgtacgacct cgtgaactcc tacaagcccg acctgatttg agcgacggc      660 gagtgggagt gccccgacac ctattggaac tccaccaact ttctgtcctg gctgtacaac     720 gactccccctg tgaaggacga ggtggtcgtg aacgacagat ggggccagaa ctgctcctgt   780
```

```
caccacggcg gctactacaa ctgcgaggac aagttcaagc cccagtccct gcccgaccac    840
aagtgggaga tgtgcacctc tatcgacaag ttctcctggg gctaccggcg ggacatggcc    900
ctgtctgatg tgaccgagga atccgagatc atctccgagc tggtgcagac cgtgtccctg    960
ggcggcaact acctgctgaa catcggccct accaaggacg gcctgatcgt gcccatcttc    1020
caggaacggc tgctggccgt gggcaagtgg ctgtctatca acggcgaggc catctacgcc    1080
tccaagcctt ggcgagtgca gtgggagaag aacaccacct ccgtgtggta cacctccaag    1140
ggctctgccg tgtacgccat cttcctgcac tggcccgaga acggcgtgct gaacctggaa    1200
tcccccatca ccacctctac caccaagatc accatgctgg gcatccaggg cgacctgaag    1260
tggtccaccg accctgacaa gggcctgttc atctccctgc ccagctgcc tccttccgct    1320 gtgcctgctg agttcgcctg gaccatcaag ctgaccggcg tgaagcacca ccaccatcac    1380
cattga                                                              1386
```

<210> SEQ ID NO 3
<211> LENGTH: 465
<212> TYPE: PRT
<213> ORGANISM: Artificial Sequence
<220> FEATURE:
<223> OTHER INFORMATION: Synthetic Polypeptide

<400> SEQUENCE: 3

```
Met Arg Val Pro Ala Gln Leu Leu Gly Leu Leu Leu Leu Trp Leu Pro
1               5                   10                  15

Gly Ala Arg Cys His Ser Ala Thr Arg Phe Asp Pro Thr Trp Glu Ser
            20                  25                  30

Leu Asp Ala Arg Gln Leu Pro Ala Trp Phe Asp Gln Ala Lys Phe Gly
        35                  40                  45

Ile Phe Ile His Trp Gly Val Phe Ser Val Pro Ser Phe Gly Ser Glu
    50                  55                  60

Trp Phe Trp Trp Tyr Trp Gln Lys Glu Lys Ile Pro Lys Tyr Val Glu
65                  70                  75                  80

Phe Met Lys Asp Asn Tyr Pro Pro Ser Phe Lys Tyr Glu Asp Phe Gly
                85                  90                  95

Pro Leu Phe Thr Ala Lys Phe Phe Asn Ala Asn Gln Trp Ala Asp Ile
            100                 105                 110

Phe Gln Ala Ser Gly Ala Lys Tyr Ile Val Leu Thr Ser Lys His His
        115                 120                 125

Glu Gly Phe Thr Leu Trp Gly Ser Glu Tyr Ser Trp Asn Trp Asn Ala
    130                 135                 140

Ile Asp Glu Gly Pro Lys Arg Asp Ile Val Lys Glu Leu Glu Val Ala
145                 150                 155                 160

Ile Arg Asn Arg Thr Asp Leu Arg Phe Gly Leu Tyr Tyr Ser Leu Phe
                165                 170                 175

Glu Trp Phe His Pro Leu Phe Leu Glu Asp Glu Ser Ser Ser Phe His
            180                 185                 190

Lys Arg Gln Phe Pro Val Ser Lys Thr Leu Pro Glu Leu Tyr Glu Leu
        195                 200                 205

Val Asn Asn Tyr Gln Pro Glu Val Leu Trp Ser Asp Gly Asp Gly Gly
    210                 215                 220

Ala Pro Asp Gln Tyr Trp Asn Ser Thr Gly Phe Leu Ala Trp Leu Tyr
225                 230                 235                 240

Asn Glu Ser Pro Val Arg Gly Thr Val Val Thr Asn Asp Arg Trp Gly
```

```
                245                 250                 255
Ala Gly Ser Ile Cys Lys His Gly Gly Phe Tyr Thr Cys Ser Asp Arg
            260                 265                 270

Tyr Asn Pro Gly His Leu Leu Pro His Lys Trp Glu Asn Cys Met Thr
        275                 280                 285

Ile Asp Lys Leu Ser Trp Gly Tyr Arg Arg Glu Ala Gly Ile Ser Asp
    290                 295                 300

Tyr Leu Thr Ile Glu Glu Leu Val Lys Gln Leu Val Glu Thr Val Ser
305                 310                 315                 320

Cys Gly Gly Asn Leu Leu Met Asn Ile Gly Pro Thr Leu Asp Gly Thr
                325                 330                 335

Ile Ser Val Val Phe Glu Glu Arg Leu Arg Gln Met Gly Ser Trp Leu
            340                 345                 350

Lys Val Asn Gly Glu Ala Ile Tyr Glu Thr His Thr Trp Arg Ser Gln
        355                 360                 365

Asn Asp Thr Val Thr Pro Asp Val Trp Tyr Thr Ser Lys Pro Lys Glu
    370                 375                 380

Lys Leu Val Tyr Ala Ile Phe Leu Lys Trp Pro Thr Ser Gly Gln Leu
385                 390                 395                 400

Phe Leu Gly His Pro Lys Ala Ile Leu Gly Ala Thr Glu Val Lys Leu
                405                 410                 415

Leu Gly His Gly Gln Pro Leu Asn Trp Ile Ser Leu Gly Gln Asn Gly
            420                 425                 430

Ile Met Val Glu Leu Pro Gln Leu Thr Ile His Gln Met Pro Cys Lys
        435                 440                 445

Trp Gly Trp Ala Leu Ala Leu Thr Asn Val Ile His His His His His
    450                 455                 460

His
465

<210> SEQ ID NO 4
<211> LENGTH: 1398
<212> TYPE: DNA
<213> ORGANISM: Artificial Sequence
<220> FEATURE:
<223> OTHER INFORMATION: Synthetic Polynucleotide

<400> SEQUENCE: 4
atgagagtgc tgctcagct gctgggactg ctgctgctgt ggctgcctgg cgctagatgc      60
cactccgcca ccagattcga ccccacctgg gagtctctgg acgccagaca gctgcccgct    120
tggtttgacc aggccaagtt cggcatcttc atccactggg gcgtgttctc cgtgcccagc    180
ttcggctctg agtggttctg gtggtactgg cagaaagaga agatccccaa atacgtggag    240
ttcatgaagg acaactaccc cccagctttt aagtacgagg acttcggccc cctgttcacc    300
gccaagttct tcaacgccaa ccagtgggcc gacatcttcc aggcctctgg cgccaagtac    360
atcgtgctga cctccaagca ccacgagggc ttcacccgtg tgggctccga gtactcctgg    420
aactggaacg ccatcgacga gggccccaag cgggacatcg tgaaagaact ggaagtggcc    480
atccggaacc ggaccgacct gagattcggc ctgtactact ccctgttcga gtggttccac    540
cccctgtttc tggaagatga gtcctccagc ttccacaagc ggcagttccc cgtgtccaag    600
accctgcccg agctgtacga gctcgtgaac aactaccagc ccgaggtgct gtggagtgac    660
ggggatggtg tgccccccga tcagtactgg aactctaccg gcttcctggc ctggctgtac    720
aacgagtctc ctgtgcgggg caccgtcgtg accaacgata gatgggcgc tggctccatc    780
```

```
tgcaagcacg gcggcttcta cacctgttcc gaccggtaca accccggcca tctgctgcct      840
cacaagtggg agaactgcat gaccatcgac aagctgtcct ggggctacag aagagaggcc      900
ggcatctccg actacctgac aatcgaggaa ctcgtgaagc agctggtgga aaccgtgtcc      960
tgcggcggca acctgctgat gaacatcggc cctaccctgg acggcaccat ctccgtggtg     1020
ttcgaggaac ggctgcggca gatgggctcc tggctgaaag tgaacggcga ggccatctac     1080
gagacacaca cctggcggtc ccagaacgac accgtgaccc tgacgtgtg gtacaccagc      1140 aagcccaaag aaaagctggt gtatgccatc ttcctgaagt ggcctacctc cggccagctg     1200
ttcctgggcc accctaaggc tatcctgggc gccaccgaag tgaaactgct gggccatgga     1260
cagcccctga actggatctc cctggaacag aacggcatca tggtggaact gccccagctg     1320
accatccatc agatgccctg caaatggggc tgggccctgg ccctgaccaa cgtgatccac     1380
catcaccacc accactga                                                   1398
```

<210> SEQ ID NO 5
<211> LENGTH: 465
<212> TYPE: PRT
<213> ORGANISM: Artificial Sequence
<220> FEATURE:
<223> OTHER INFORMATION: Synthetic Polypeptide

<400> SEQUENCE: 5

```
Met Arg Val Pro Ala Gln Leu Leu Gly Leu Leu Leu Leu Trp Leu Pro
  1               5                  10                  15

Gly Ala Arg Cys Lys Ser Ser Arg Arg Tyr Asp Pro Thr Trp Glu Ser
             20                  25                  30

Leu Asp Arg Arg Pro Leu Pro Ser Trp Phe Asp Gln Ala Lys Phe Gly
         35                  40                  45

Ile Phe Ile His Trp Gly Val Phe Ser Val Pro Ser Phe Gly Ser Glu
     50                  55                  60

Trp Phe Trp Trp Tyr Trp Gln Lys Glu Lys Arg Pro Lys Phe Val Asp
 65                  70                  75                  80

Phe Met Asn Asn Asn Tyr Pro Pro Gly Phe Lys Tyr Glu Asp Phe Gly
                 85                  90                  95

Val Leu Phe Thr Ala Lys Phe Phe Asn Ala Ser Gln Trp Ala Asp Ile
            100                 105                 110

Leu Gln Ala Ser Gly Ala Lys Tyr Leu Val Leu Thr Ser Lys His His
        115                 120                 125

Glu Gly Phe Thr Leu Trp Gly Ser Glu Tyr Ser Trp Asn Trp Asn Ala
    130                 135                 140

Val Asp Glu Gly Pro Lys Arg Asp Ile Val Lys Glu Leu Lys Val Ala
145                 150                 155                 160

Ile Thr Lys Asn Thr Asp Leu Arg Phe Gly Leu Tyr Tyr Ser Leu Phe
                165                 170                 175

Glu Trp Phe His Pro Leu Phe Leu Glu Asp Lys Leu Ser Ser Phe Gln
            180                 185                 190

Lys Arg Gln Phe Pro Ile Ser Lys Met Leu Pro Glu Leu Tyr Glu Leu
        195                 200                 205

Val Asn Lys Tyr Gln Pro Asp Ile Leu Trp Thr Gly Asp Gly Gly
    210                 215                 220

Ala Pro Asp Arg Tyr Trp Asn Ser Thr Gly Phe Leu Ala Trp Leu Tyr
225                 230                 235                 240

Asn Glu Ser Pro Val Arg Asn Thr Val Val Thr Asn Asp Arg Trp Gly
```

```
            245                 250                 255
Ala Gly Ser Ile Cys Lys His Gly Gly Tyr Tyr Thr Cys Ser Asp Arg
            260                 265                 270

Tyr Asn Pro Gly His Leu Leu Pro His Lys Trp Glu Asn Cys Met Thr
        275                 280                 285

Ile Asp Gln Phe Ser Trp Gly Tyr Arg Arg Glu Ala Val Ile Ser Asp
    290                 295                 300

Tyr Leu Thr Ile Glu Glu Leu Val Lys Gln Leu Val Glu Thr Val Ala
305                 310                 315                 320

Cys Gly Gly Asn Leu Leu Met Asn Ile Gly Pro Thr Leu Asp Gly Ile
                325                 330                 335

Ile Pro Val Ile Phe Glu Glu Arg Leu Arg Gln Met Gly Met Trp Leu
            340                 345                 350

Lys Val Asn Gly Glu Ala Ile Tyr Glu Thr Gln Pro Trp Arg Ser Gln
        355                 360                 365

Asn Asp Thr Ala Thr Pro Asp Val Trp Tyr Thr Tyr Lys Pro Glu Glu
    370                 375                 380

Lys Ile Val Tyr Ala Ile Phe Leu Lys Trp Pro Val Ser Arg Glu Leu
385                 390                 395                 400

Phe Leu Glu Gln Pro Ile Gly Ser Leu Gly Glu Thr Glu Val Ala Leu
                405                 410                 415

Leu Gly Glu Gly Lys Pro Leu Trp Thr Ser Leu Lys Pro Asn Gly
            420                 425                 430

Ile Ile Val Glu Leu Pro Gln Leu Thr Leu His Gln Met Pro Cys Lys
        435                 440                 445

Trp Gly Trp Thr Leu Ala Leu Thr Asn Val Thr His His His His
    450                 455                 460

His
465

<210> SEQ ID NO 6
<211> LENGTH: 1398
<212> TYPE: DNA
<213> ORGANISM: Artificial Sequence
<220> FEATURE:
<223> OTHER INFORMATION: Synthetic Polynucleotide

<400> SEQUENCE: 6
atgagagtgc tgctcagct gctgggactg ctgctgctgt ggctgcctgg cgctagatgc      60
aagtcctctc ggagatacga ccccacctgg gagtccctgg acagaaggcc tctgcccagt    120
tggttcgacc aggccaagtt cggcatcttc atccactggg gcgtgttctc cgtgcccagc    180
ttcggctctg agtggttctg gtggtactgg cagaaagaga gcggcccaa gttcgtggac     240 ttcatgaaca caactaccc ccctggcttt aagtacgagg acttcggcgt gctgttcacc    300
gccaagttct tcaacgcctc ccagtgggcc gacatcctgc aggcttccgg cgctaagtac    360
ctggtgctga cctccaagca ccacgagggc tttaccctgt ggggctccga gtactcctgg    420
aactggaacg ccgtggacga gggccctaag cgggacatcg tgaaagaact gaaggtggcc    480
atcaccaaga acaccgacct gagattcggc ctgtactact ccctgttcga gtggttccac    540 ccctgttc tggaagataa gctgtccagc ttccagaagc ggcagttccc catctccaag     600
atgctgcccg agctgtacga gctcgtgaac aagtaccagc tgacatcct gtggaccgac    660 ggggatggtg gcgcccctga cagatactgg aactctaccg gcttcctggc ctggctgtac    720
aacgagtccc ctgtgcggaa caccgtcgtg accaacgaca gatggggcgc tggctccatc    780
```

```
tgcaagcacg gcggctacta cacctgttcc gaccggtaca accccggcca tctgctgcct    840
cacaagtggg agaactgcat gacaatcgac cagttctcct ggggctaccg gcgcgaggcc    900
gtgatctctg actacctgac catcgaggaa ctcgtgaagc agctggtgga aaccgtggcc    960
tgtggcggca acctgctgat gaacatcggc cctaccctgg acggcatcat ccccgtgatc   1020
ttcgaggaac ggctgcggca gatgggcatg tggctgaaag tgaacggcga ggccatctac   1080
gagacacagc cttggcggtc ccagaacgac accgccacac tgacgtgtg gtacacctac    1140 aagcccgaag agaagatcgt gtacgccatc ttcctgaagt ggcccgtgtc cagagagctg   1200
tttctggaac agcccatcgg ctccctgggc gagacagaag tggctctgct gggcgagggc   1260
aagcctctga cctggacctc cctgaagccc aatggcatca tcgtggaact gccccagctg   1320
accctgcacc agatgccctg taaatggggc tggaccctgg ccctgaccaa cgtgacccac   1380
caccaccatc accactga                                                 1398
```

<210> SEQ ID NO 7
<211> LENGTH: 481
<212> TYPE: PRT
<213> ORGANISM: Artificial Sequence
<220> FEATURE:
<223> OTHER INFORMATION: Synthetic Polypeptide

<400> SEQUENCE: 7

```
Met Arg Val Pro Ala Gln Leu Leu Gly Leu Leu Leu Leu Trp Leu Pro
1               5                   10                  15

Gly Ala Arg Cys His Asn Val Ser Glu Gly Tyr Glu Lys Pro Ala Asp
            20                  25                  30

Pro Leu Val Val Gln Asn Leu Glu Gln Trp Gln Asp Leu Lys Phe Gly
        35                  40                  45

Leu Phe Met His Trp Gly Thr Tyr Ser Gln Trp Gly Ile Val Glu Ser
    50                  55                  60

Trp Ser Leu Cys Pro Glu Asp Glu Ser Trp Thr Gln Arg Lys Pro Glu
65                  70                  75                  80

His Gly Lys Ser Tyr Asn Glu Tyr Val Lys Asn Tyr Glu Asn Leu Gln
                85                  90                  95

Thr Thr Phe Asn Pro Val Gln Phe Asn Pro Gln Lys Trp Ala Asp Ala
            100                 105                 110

Thr Lys Lys Ala Gly Met Lys Tyr Val Val Phe Thr Thr Lys His His
        115                 120                 125

Asp Gly Phe Ala Met Phe Asp Thr Lys Gln Ser Asp Tyr Lys Ile Thr
    130                 135                 140

Ser Ser Lys Thr Pro Phe Ser Lys Asn Pro Lys Ala Asp Val Ala Lys
145                 150                 155                 160

Glu Ile Phe Asn Thr Phe Arg Asp Asn Gly Phe Arg Ile Gly Ala Tyr
                165                 170                 175

Phe Ser Lys Pro Asp Trp His Ser Asp Asp Tyr Trp Trp Ser Tyr Phe
            180                 185                 190

Pro Pro Lys Asp Arg Asn Val Asn Tyr Asp Pro Gln Lys Tyr Pro Ala
        195                 200                 205

Arg Trp Glu Asn Phe Lys Lys Phe Thr Phe Asn Gln Leu Asn Glu Ile
    210                 215                 220

Thr Ser Asn Tyr Gly Lys Ile Asp Ile Leu Trp Leu Asp Gly Gly Trp
225                 230                 235                 240

Val Arg Pro Phe His Thr Ile Asp Pro Asn Ile Glu Trp Gln Arg Thr
```

```
                245                 250                 255
Ile Lys Val Glu Gln Asp Ile Asp Met Asp Lys Ile Gly Thr Met Ala
            260                 265                 270
Arg Lys Asn Gln Pro Gly Ile Ile Val Asp Arg Thr Val Pro Gly
        275                 280                 285
Lys Trp Glu Asn Tyr Val Thr Pro Glu Gln Ala Val Pro Glu His Ala
        290                 295                 300
Leu Ser Ile Pro Trp Glu Ser Cys Ile Thr Met Gly Asp Ser Phe Ser
305                 310                 315                 320
Tyr Val Pro Asn Asp Asn Tyr Lys Ser Gln Lys Ile Ile Glu Thr
                325                 330                 335
Leu Ile Arg Ile Ile Ser Arg Gly Gly Asn Tyr Leu Met Asn Ile Ala
                340                 345                 350
Pro Gly Pro Asn Gly Asp Tyr Asp Ala Val Val Tyr Glu Arg Leu Lys
            355                 360                 365
Glu Ile Ser Gly Trp Met Asp Lys Asn Gln Ser Ala Val Phe Thr Thr
        370                 375                 380
Arg Ala Leu Ala Pro Tyr His Glu Ser Asp Phe Tyr Tyr Thr Gln Ser
385                 390                 395                 400
Lys Asp Gly Lys Ile Val Asn Val Phe His Ile Ser Glu Lys Ser Asn
                405                 410                 415
Tyr Gln Ala Pro Ser Glu Leu Ser Phe Ser Ile Pro Gly Asn Ile Asn
            420                 425                 430
Pro Lys Thr Val Lys Val Leu Gly Ile Ser Ser Gln Ile Lys Trp Lys
        435                 440                 445
Lys Lys Gly Asn Lys Ile His Val Gln Leu Pro Glu Glu Arg Thr Lys
        450                 455                 460
Leu Asn Tyr Ser Thr Val Ile Gln Ile Thr Gln His His His His
465                 470                 475                 480
His
```

<210> SEQ ID NO 8
<211> LENGTH: 1446
<212> TYPE: DNA
<213> ORGANISM: Artificial Sequence
<220> FEATURE:
<223> OTHER INFORMATION: Synthetic Polynucleotide

<400> SEQUENCE: 8

```
atgagagtgc tgctcagct gctgggactg ctgctgctgt ggctgcctgg cgctagatgc      60
cacaatgtgt ccgagggcta cgagaagccc gccgaccctc tggtggtgca gaacctggaa    120
cagtggcagg acctgaagtt cggcctgttc atgcactggg caccactctc ccagtggggc    180
atcgtggaat cctggtccct gtgccctgag acgagtctt ggacccagcg gaagcctgag     240
cacggcaagt cctacaacga gtacgtgaag aactacgaga acctgcagac cacccttcaac   300
cccgtgcagt tcaacccca gaagtgggcc gacgccacca gaaagccgg catgaaatac     360
gtggtgttca ccaccaagca ccacgacggc ttcgccatgt tcgacaccaa gcagtccgac    420
tacaagatca cctcctccaa gacccccttc agcaagaacc caaggccga cgtggccaaa    480
gagattttca cacccttccg ggacaacggc ttccggatcg gcgcctactt ctccaagcct    540
gactggcact ccgacgacta ctggtggtcc tacttcccac ccaaggaccg gaacgtgaac    600
tacgaccctc agaaataccc cgccagatgg gagaacttca gaagttcac cttcaatcag    660
ctgaacgaga tcaccagcaa ctacggcaag atcgacatcc tgtggctgga cggcggatgg   720
```

-continued

```
gtgcgaccct tccacaccat cgaccccaac atcgagtggc agcggaccat caaggtggaa      780
caggacatcg acatggacaa gatcggcacc atggcccgga agaaccagcc cggcatcatc      840
atcgtggacc ggaccgtgcc tggcaagtgg agaattacg tgaccccga gcaggccgtg       900 cctgagcatg ccctgtctat cccttgggag tcctgtatca aatgggcga cagcttctcc      960 tacgtgccca cgacaactac aagtcctcc cagaagatca tcgagacact gatcaggatc     1020
atctccagag gcggcaacta cctgatgaat atcgccctg ccccaacgg cgactacgac      1080 gctgtggtgt acgagcggct gaaagaaatc tccggctgga tggataagaa ccagtccgcc     1140
gtgtttacca cccgggctct ggccccttac cacgagtccg acttctacta cacccagtcc     1200
aaggacggaa agatcgtgaa cgtgttccac atctccgaga gtccaacta ccaggccccc     1260 tccgagctgt ccttcagcat ccccgagaac atcaaccca agaccgtgaa ggtgctgggc     1320
atctccagcc agatcaagtg gaagaagaag ggcaacaaga tccacgtgca gctgcccgag     1380
gaacggacca gctgaactac ctccaccgtg atccagatca cccagcacca ccaccatcac     1440
cactga                                                               1446
```

<210> SEQ ID NO 9
<211> LENGTH: 440
<212> TYPE: PRT
<213> ORGANISM: Artificial Sequence
<220> FEATURE:
<223> OTHER INFORMATION: Synthetic Polypeptide

<400> SEQUENCE: 9

```
Met Arg Val Pro Ala Gln Leu Leu Gly Leu Leu Leu Leu Trp Leu Pro
1               5                   10                  15

Gly Ala Arg Cys Gln Gln Lys Tyr Gln Pro Thr Glu Ala Asn Leu Lys
            20                  25                  30

Ala Arg Ser Glu Phe Gln Asp Asn Lys Phe Gly Ile Phe Leu His Trp
        35                  40                  45

Gly Leu Tyr Ala Met Leu Ala Thr Gly Glu Trp Thr Met Thr Asn Asn
    50                  55                  60

Asn Leu Asn Tyr Lys Glu Tyr Ala Lys Leu Ala Gly Gly Phe Tyr Pro
65                  70                  75                  80

Ser Lys Phe Asp Ala Asp Lys Trp Val Ala Ala Ile Lys Ala Ser Gly
                85                  90                  95

Ala Lys Tyr Ile Cys Phe Thr Thr Arg His His Glu Gly Phe Ser Met
            100                 105                 110

Phe Asp Thr Lys Tyr Ser Asp Tyr Asn Ile Val Lys Ala Thr Pro Phe
        115                 120                 125

Lys Arg Asp Val Val Lys Glu Leu Ala Asp Ala Cys Ala Lys His Gly
    130                 135                 140

Ile Lys Leu His Phe Tyr Tyr Ser His Ile Asp Trp Tyr Arg Glu Asp
145                 150                 155                 160

Ala Pro Gln Gly Arg Thr Gly Arg Arg Thr Gly Arg Pro Asn Pro Lys
                165                 170                 175

Gly Asp Trp Lys Ser Tyr Tyr Gln Phe Met Asn Asn Gln Leu Thr Glu
            180                 185                 190

Leu Leu Thr Asn Tyr Gly Pro Ile Gly Ala Ile Trp Phe Asp Gly Trp
        195                 200                 205

Trp Asp Gln Asp Ile Asn Pro Asp Phe Asp Trp Glu Leu Pro Glu Gln
    210                 215                 220
```

Tyr Ala Leu Ile His Arg Leu Gln Pro Ala Cys Leu Val Gly Asn Asn
225                 230                 235                 240

His His Gln Thr Pro Phe Ala Gly Glu Asp Ile Gln Ile Phe Glu Arg
            245                 250                 255

Asp Leu Pro Gly Glu Asn Thr Ala Gly Leu Ser Gly Gln Ser Val Ser
            260                 265                 270

His Leu Pro Leu Glu Thr Cys Glu Thr Met Asn Gly Met Trp Gly Tyr
            275                 280                 285

Lys Ile Thr Asp Gln Asn Tyr Lys Ser Thr Lys Thr Leu Ile His Tyr
        290                 295                 300

Leu Val Lys Ala Ala Gly Lys Asp Ala Asn Leu Leu Met Asn Ile Gly
305                 310                 315                 320

Pro Gln Pro Asp Gly Glu Leu Pro Glu Val Ala Val Gln Arg Leu Lys
            325                 330                 335

Glu Val Gly Glu Trp Met Ser Lys Tyr Gly Glu Thr Ile Tyr Gly Thr
            340                 345                 350

Arg Gly Gly Leu Val Ala Pro His Asp Trp Gly Val Thr Thr Gln Lys
            355                 360                 365

Gly Asn Lys Leu Tyr Val His Ile Leu Asn Leu Gln Asp Lys Ala Leu
        370                 375                 380

Phe Leu Pro Ile Val Asp Lys Val Lys Lys Ala Val Val Phe Ala
385                 390                 395                 400

Asp Lys Thr Pro Val Arg Phe Thr Lys Asn Lys Glu Gly Ile Val Leu
            405                 410                 415

Glu Leu Ala Lys Val Pro Thr Asp Val Asp Tyr Val Val Glu Leu Thr
            420                 425                 430

Ile Asp His His His His His His
        435                 440

<210> SEQ ID NO 10
<211> LENGTH: 1323
<212> TYPE: DNA
<213> ORGANISM: Artificial Sequence
<220> FEATURE:
<223> OTHER INFORMATION: Synthetic Polynucleotide

<400> SEQUENCE: 10

```
atgagagtgc tgctcagct gctgggactg ctgctgctgt ggctgcctgg tgctagatgc      60
cagcagaagt accagcccac cgaggccaac ctgaaggcca gatccgagtt ccaggacaac     120
aagttcggca tcttcctgca ctggggccct tacgccatgc tggctactgg cgagtggacc     180
atgaccaaca caacctgaa ctacaaagag tacgctaagc tggctggcgg cttctacccc     240
tccaagttcg acgccgacaa atgggtggcc gccatcaagg cctctggcgc caagtacatc     300
tgcttcacca cccggcacca cgagggcttc tccatgttcg acaccaagta ctccgactac     360
aacatcgtga aggccacccc cttcaagcgg gacgtcgtga agagctggc cgacgcctgc     420
gctaagcacg gcatcaagct gcacttctac tactcccaca tcgactggta cagagaggac     480
gcccccagg gcagaaccgg cagaagaaca ggcagaccca cccccaaggg cgactggaag     540
tcctactacc agtttatgaa caaccagctg accgagctgc tgaccaacta cggccccatc     600
ggcgccattt ggttcgacgg tgtggtggac caggacatca accccgactt cgactgggag     660
ctgccgagc agtacgccct gatccacaga ctgcagcccg cctgtctcgt gggcaacaac     720
caccaccaga ccccctttgc cggcgaggac atccagattt tcgagcggga tctgcccggc     780
gagaacaccg ctggactgtc tggccagtcc gtgtcccatc tgcccctgga aacctgcgag     840
```

```
acaatgaacg gcatgtgggg ctacaagatc accgaccaga actacaagtc caccaagaca    900
ctgatccact acctcgtgaa agccgctggc aaggacgcca acctgctgat gaacatcggc    960
ccccagcctg acggcgagct gcctgaagtg gctgtgcagc ggctgaaaga agtgggagag   1020
tggatgtcta agtacggcga gactatctac ggcaccagag gcggcctggt ggcccctcat   1080
gattggggcg tgaccaccca gaagggcaac aagctgtacg tgcacatcct gaacctgcag   1140
gacaaggccc tgttcctgcc catcgtggac aagaaagtga agaaagccgt ggtgttcgcc   1200
gacaagaccc ccgtgcggtt caccaagaac aaagagggca tcgtgctgga actggccaag   1260
gtgcccaccg acgtggacta cgtggtggaa ctgaccatcg accaccatca tcaccaccac   1320
tga                                                                 1323
```

<210> SEQ ID NO 11
<211> LENGTH: 920
<212> TYPE: PRT
<213> ORGANISM: Artificial Sequence
<220> FEATURE:
<223> OTHER INFORMATION: Synthetic Polypeptide

<400> SEQUENCE: 11

```
Met Arg Val Pro Ala Gln Leu Leu Gly Leu Leu Leu Leu Trp Leu Pro
1               5                   10                  15

Gly Ala Arg Cys Ala Gln His Asp Ser Leu Ile Arg Val Lys Ala Glu
            20                  25                  30

Asp Lys Val Val Gln Thr Ser Pro Ser Val Ser Ala Ile Asp Asp Leu
        35                  40                  45

His Tyr Leu Ser Glu Asn Ser Lys Lys Glu Phe Lys Glu Gly Leu Ser
    50                  55                  60

Lys Ala Gly Glu Val Pro Glu Lys Leu Lys Asp Ile Leu Ser Lys Ala
65                  70                  75                  80

Gln Gln Ala Asp Lys Gln Ala Lys Val Leu Ala Glu Met Lys Val Pro
                85                  90                  95

Glu Lys Ile Ala Met Lys Pro Leu Lys Gly Pro Leu Tyr Gly Gly Tyr
            100                 105                 110

Phe Arg Thr Trp His Asp Lys Thr Ser Asp Pro Ala Glu Lys Asp Lys
        115                 120                 125

Val Asn Ser Met Gly Glu Leu Pro Lys Glu Val Asp Leu Ala Phe Val
    130                 135                 140

Phe His Asp Trp Thr Lys Asp Tyr Ser Leu Phe Trp Gln Glu Leu Ala
145                 150                 155                 160

Thr Lys His Val Pro Thr Leu Asn Lys Gln Gly Thr Arg Val Ile Arg
                165                 170                 175

Thr Ile Pro Trp Arg Phe Leu Ala Gly Gly Asp His Ser Gly Ile Ala
            180                 185                 190

Glu Asp Thr Gln Lys Tyr Pro Asn Thr Pro Glu Gly Asn Lys Ala Leu
        195                 200                 205

Ala Lys Ala Ile Val Asp Glu Tyr Val Tyr Lys Tyr Asn Leu Asp Gly
    210                 215                 220

Leu Asp Val Asp Ile Glu Arg Asp Ser Ile Pro Lys Val Asn Gly Lys
225                 230                 235                 240

Glu Ser Asn Glu Asn Ile Gln Arg Ser Ile Ala Val Phe Glu Glu Ile
                245                 250                 255

Gly Lys Leu Ile Gly Pro Lys Gly Ala Asp Lys Ser Arg Leu Phe Ile
            260                 265                 270
```

```
Met Asp Ser Thr Tyr Met Ala Asp Lys Asn Pro Leu Ile Glu Arg Gly
            275                 280                 285
Ala Pro Tyr Ile Asp Leu Leu Leu Val Gln Val Tyr Gly Ile Gln Gly
290                 295                 300
Glu Lys Gly Asp Trp Asp Pro Val Ala Arg Lys Pro Glu Lys Thr Met
305                 310                 315                 320
Glu Glu Arg Trp Glu Ser Tyr Ser Lys Tyr Ile Arg Pro Gln Tyr
                325                 330                 335
Met Val Gly Phe Ser Phe Tyr Glu Glu Asn Ala Gly Ser Gly Asn Leu
            340                 345                 350
Trp Tyr Asp Ile Asn Glu Arg Lys Asp His Asn Pro Leu Asn Ser
            355                 360                 365
Glu Ile Ala Gly Thr Arg Ala Glu Arg Tyr Ala Lys Trp Gln Pro Lys
    370                 375                 380
Thr Gly Gly Val Lys Gly Gly Ile Phe Ser Tyr Ala Ile Asp Arg Asp
385                 390                 395                 400
Gly Val Ala His Gln Pro Lys Lys Val Ser Asp Glu Lys Arg Thr
                405                 410                 415
Asn Lys Ala Ile Lys Asp Ile Thr Asp Gly Ile Val Lys Ser Asp Tyr
                420                 425                 430
Lys Val Ser Lys Ala Leu Lys Lys Val Met Glu Asn Asp Lys Ser Tyr
            435                 440                 445
Glu Leu Ile Asp Gln Lys Asp Phe Pro Asp Lys Ala Leu Arg Glu Ala
    450                 455                 460
Val Ile Ala Gln Val Gly Ser Arg Arg Gly Asp Leu Glu Arg Phe Asn
465                 470                 475                 480
Gly Thr Leu Arg Leu Asp Asn Pro Asp Ile Lys Ser Leu Glu Gly Leu
                485                 490                 495
Asn Lys Leu Lys Lys Leu Ala Lys Leu Glu Leu Ile Gly Leu Ser Gln
                500                 505                 510
Ile Thr Lys Leu Asp Ser Ser Val Leu Pro Glu Asn Ile Lys Pro Thr
            515                 520                 525
Lys Asp Thr Leu Val Ser Val Leu Glu Thr Tyr Lys Asn Asp Asp Arg
            530                 535                 540
Lys Glu Glu Ala Lys Ala Ile Pro Gln Val Ala Leu Thr Ile Ser Gly
545                 550                 555                 560
Leu Thr Gly Leu Lys Glu Leu Asn Leu Ala Gly Phe Asp Arg Asp Ser
                565                 570                 575
Leu Ala Gly Ile Asp Ala Ala Ser Leu Thr Ser Leu Glu Lys Val Asp
            580                 585                 590
Leu Ser Lys Asn Lys Leu Asp Leu Ala Ala Gly Thr Glu Asn Arg Gln
            595                 600                 605
Ile Phe Asp Val Met Leu Ser Thr Val Ser Asn Arg Val Gly Ser Asn
    610                 615                 620
Glu Gln Thr Val Thr Phe Asp His Gln Lys Pro Thr Gly His Tyr Pro
625                 630                 635                 640
Asn Thr Tyr Gly Thr Thr Ser Leu Arg Leu Pro Val Gly Glu Gly Lys
                645                 650                 655
Ile Asp Leu Gln Ser Gln Leu Leu Phe Gly Thr Val Thr Asn Gln Gly
                660                 665                 670
Thr Leu Ile Asn Ser Glu Ala Asp Tyr Lys Ala Tyr Gln Glu Gln Leu
            675                 680                 685
```

```
Ile Ala Gly Arg Arg Phe Val Asp Pro Gly Tyr Ala Tyr Lys Asn Phe
    690                 695                 700
Ala Val Thr Tyr Asp Ala Tyr Lys Val Arg Val Thr Asp Ser Thr Leu
705                 710                 715                 720
Gly Val Thr Asp Glu Lys Lys Leu Ser Thr Ser Lys Glu Glu Thr Tyr
                725                 730                 735
Lys Val Glu Phe Phe Ser Pro Thr Asn Gly Thr Lys Pro Val His Glu
            740                 745                 750
Ala Lys Val Val Gly Ala Glu Lys Thr Met Met Val Asn Leu Ala
        755                 760                 765
Ala Gly Ala Thr Val Ile Lys Ser Asp Ser His Glu Asn Ala Lys Lys
770                 775                 780
Val Phe Asp Gly Ala Ile Glu Tyr Asn Pro Leu Ser Phe Ser Ser Lys
785                 790                 795                 800
Thr Ser Ile Thr Phe Glu Phe Lys Glu Pro Gly Leu Val Lys Tyr Trp
                805                 810                 815
Arg Phe Phe Asn Asp Ile Thr Arg Lys Asp Asp Tyr Ile Lys Glu Ala
            820                 825                 830
Lys Leu Glu Ala Phe Val Gly His Leu Glu Asp Asp Ser Lys Val Lys
        835                 840                 845
Asp Ser Leu Glu Lys Ser Thr Glu Trp Val Thr Val Ser Asp Tyr Ser
850                 855                 860
Gly Glu Ala Gln Glu Phe Ser Gln Pro Leu Asp Asn Ile Ser Ala Lys
865                 870                 875                 880
Tyr Trp Arg Val Thr Val Asp Thr Lys Gly Gly Arg Tyr Ser Ser Pro
                885                 890                 895
Ser Leu Pro Glu Leu Gln Ile Leu Gly Tyr Arg Leu Pro Leu Thr His
            900                 905                 910
Asp Tyr Lys Asp Asp Asp Asp Lys
        915                 920

<210> SEQ ID NO 12
<211> LENGTH: 2763
<212> TYPE: DNA
<213> ORGANISM: Artificial Sequence
<220> FEATURE:
<223> OTHER INFORMATION: Synthetic Polynucleotide

<400> SEQUENCE: 12
atgagagtgc ctgctcagct gctgggcctg ctgctgctgt ggctgcctgg tgctagatgc      60
gcccagcacg actccctgat cagagtgaag gccgaggaca ggtggtgca gacctcccct     120 tccgtgtccg ccatcgacga cctgcactac ctgtccgaga actccaagaa agagttcaaa    180
gagggcctgt ccaaggccgg cgaggtgccc gaaaagctga aggacatcct gagcaaggct    240
cagcaggccg acaagcaggc caaggtgctg gccgagatga aggtgccaga agatcgcc     300 atgaagcccc tgaagggccc tctgtacggc ggctacttca gaacctggca cgacaagacc    360
tccgaccccg ccgagaagga caaagtgaac tccatgggcg agctgcccaa agaggtggac    420
ctggccttcg tgttccacga ctggaccaag gactactccc tgttctggca ggaactggcc    480
accaagcacg tgcccaccct gaacaagcag ggcaccagtg atccggac aatcccctgg     540 cggtttctgg ctggcggcga ccactctgga atcgccgagg ataccagaa gtaccccaac    600 acccccgagg gcaacaaggc cctggctaag gccatcgtgg acgagtacgt gtacaagtac    660
aacctggacg gcctggacgt ggacatcgag cgggactcca tccctaaagt gaacggcaaa    720
```

-continued

```
gagtccaacg agaacatcca gcggtctatc gccgtgttcg aggaaatcgg caagctgatc      780
ggccccaagg gcgccgacaa gtcccggctg ttcatcatgg actccaccta catggccgat      840
aagaaccccc tgatcgagag aggcgcccct tacatcgatc tgctgctggt gcaggtgtac      900
ggcatccagg gcgagaaggg cgattgggac cctgtggccc ggaagcctga aaagaccatg      960
gaagagagat gggagtccta ctccaagtac atccggcccg agcagtatat ggtgggattc     1020
agcttctacg aggaaaacgc cggctccggc aacctgtggt acgacatcaa cgagcggaag     1080
gacgaccaca accctctgaa ctccgagatc gccggcaccc gggctgagag atacgctaag     1140
tggcagccca agaccggcgg agtgaagggc ggcatcttct cctacgccat cgatagggat     1200
ggcgtggccc accagcctaa gaaggtgtcc gacgacgaga gcggaccaa caaggctatc     1260 aaggacatca ccgacggcat cgtgaagtcc gactacaagg tgtccaaagc cctgaagaaa     1320
gtgatggaaa cgacaagag ctacgagctg atcgaccaga aggacttccc cgataaggcc     1380
ctgcgcgagg ccgtgattgc tcaagtgggc tccagacggg gcgacctgga aagattcaac     1440 ggcacctgc ggctggacaa ccccgacatc aagtccctgg aaggcctgaa caaactgaag     1500
aagctggcca agctggaact gatcggactg tcccagatca caaagctgga ctcctccgtg     1560
ctgcctgaga acatcaagcc caccaaggac accctggtgt ccgtgctgga aacctacaag     1620
aacgacgacc ggaaagagga agccaaggcc atccctcagg tggccctgac catctctggc     1680
ctgaccggcc tgaaagagct gaatctggcc ggcttcgacc gggattccct ggctggaatc     1740
gatgccgcct ctctgacctc cctggaaaaa gtggacctgt ctaagaacaa gctggatctg     1800
gctgccggca ccgagaaccg gcagatcttc gacgtgatgc tgtccaccgt gtccaacaga     1860
gtgggcagca acgagcagac cgtgaccttc gaccaccaga agcccaccgg ccactaccct     1920
aacacctacg gcaccacctc cctgagactg cctgtgggcg agggcaagat cgacctgcag     1980
tcccagctgc tgttcggcac cgtgaccaac cagggcacac tgatcaactc cgaggccgat     2040
tacaaggcct accaggaaca gctgatcgct gggcggagat cgtggacccc tggctacgct     2100
tacaagaact cgccgtgac ctacgatgcc tacaaagtgc gcgtgaccga ctccaccctg     2160
ggcgtgacag acgaaaagaa gctgagcacc tccaagaag agacatacaa ggtggaattc     2220
ttctccccca ccaatggcac caagcctgtg catgaggcta aggtggtcgt gggcgccgag     2280
aaaaccatga tggtcaacct ggccgctggc gccaccgtga tcaagtctga ctctcacgag     2340
aatgccaaaa aggtgttcga cggcgccatc gagtacaatc tctctgagctt ctccagcaag     2400 accagcatca ccttcgagtt taaagaaccc ggcctcgtga atactggcg gttcttcaac     2460 gatatcaccc gcaaggacga ctacatcaaa gaggctaagc tggaagcctt cgtgggccat     2520
ctggaagatg actccaaagt gaaggactct ctggaaaagt ccaccgagtg ggtcaccgtg     2580
tctgactact ctggcgaggc ccaggaattc tcccagcccc tggacaacat ctccgccaag     2640
tattggagag tgaccgtgga caccaagggc ggacggtaca gctctcctag cctgcccgag     2700
ctgcagatcc tgggctacag actgcctctg acccacgact ataaggacga cgacgacaaa     2760
tga                                                                  2763
```